United States Patent
Zhang et al.

(10) Patent No.: US 11,497,206 B2
(45) Date of Patent: Nov. 15, 2022

(54) CELL CRYOPRESERVATION PROTECTIVE COMPOSITION AND USE THEREOF

(71) Applicant: Tianjin University, Tianjin (CN)

(72) Inventors: Lei Zhang, Tianjin (CN); Jing Yang, Tianjin (CN)

(73) Assignee: Tianjin University, Tianjin (CN)

( * ) Notice: Subject to any disclaimer, the term of this patent is extended or adjusted under 35 U.S.C. 154(b) by 1091 days.

(21) Appl. No.: 16/087,617

(22) PCT Filed: Apr. 7, 2017

(86) PCT No.: PCT/CN2017/079744
§ 371 (c)(1),
(2) Date: Sep. 21, 2018

(87) PCT Pub. No.: WO2017/174032
PCT Pub. Date: Oct. 12, 2017

(65) Prior Publication Data
US 2019/0037832 A1     Feb. 7, 2019

(30) Foreign Application Priority Data
Apr. 8, 2016 (CN) .......................... 201610223983.4

(51) Int. Cl.
*A01N 1/02*       (2006.01)
*C07C 229/22*   (2006.01)
*C07C 237/50*   (2006.01)
*C12N 5/095*     (2010.01)

(52) U.S. Cl.
CPC .......... *A01N 1/0221* (2013.01); *C07C 229/22* (2013.01); *C07C 237/50* (2013.01); *C12N 5/0695* (2013.01)

(58) Field of Classification Search
None
See application file for complete search history.

(56) References Cited

U.S. PATENT DOCUMENTS

| 5,879,875 A | 3/1999 | Wiggins et al. | |
| 6,361,933 B1 * | 3/2002 | Wiggins | A01N 1/0226 435/1.3 |
| 2004/0229203 A1 * | 11/2004 | Wiggins | A01N 1/0221 435/1.1 |
| 2016/0106091 A1 * | 4/2016 | Meunier | A01N 3/00 435/420 |
| 2019/0037832 A1 * | 2/2019 | Zhang | C07C 237/50 |

FOREIGN PATENT DOCUMENTS

| CN | 104161036 A | 11/2014 |
| CN | 105685016 A | 6/2016 |
| CN | 106342787 A | 1/2017 |
| FI | 884758 A | 4/1989 |
| JP | 2014150777 A | 8/2014 |
| WO | WO 2007/149142 A1 | 12/2007 |

OTHER PUBLICATIONS

Yang, J. et al. Natural Zwitterionic Betaine Enables Cells to Survive Ultrarapid Cryopreservation. Scientific Reports1-9, Nov. 22, 2016. (Year: 2016).*
International Search Report from International Patent Application No. PCT/CN2017/079744 dated Jul. 11, 2017, application now published as International Publication No. WO2017/174032 published Oct. 12, 2017.
Written Opinion from International Patent Application No. PCT/CN2017/079744 dated Jul. 11, 2017, application now published as International Publication No. WO2017/174032 published Oct. 12, 2017 *Chinese Language Only*.

* cited by examiner

*Primary Examiner* — Ralph J Gitomer
(74) *Attorney, Agent, or Firm* — McDermott Will and Emery LLP; Judy Mohr; J. Wendy Davis

(57) ABSTRACT

The present application relates to a cell cryopreservation protective composition, the use of the composition, and a cell cryopreservation method. The cell cryopreservation protective composition comprises a zwitterionic molecule having the general formula $R_1$—$N^+(CH_3)_2$—$(CH_2)_n$—$R_2$, wherein $R_1$ is a linear or branched alkyl having 1 to 10 carbon atoms, and is optionally substituted with a substituent; $R_2$ is any negatively charged group selected from the group consisting of —$COO^-$, —$SO_4^-$, —$SO_3^-$, and (I); and $R_3$ is a group selected from the group consisting of (methyl)acryloyloxyalkyl, alkyl and alkenyl; and the zwitterionic molecule having general formula $R_1$—$N^+(CH_3)_2$—$(CH_2)_n$—$R_2$ is preferably a betaine compound. The cell cryopreservation protective composition can carry out cell cryopreservation in a non-toxic and efficient manner, and results in an extremely high post-thaw cell survival rate and does not require stepwise cryopreservation. After cell recovery, the cells can be used directly or after being slightly diluted.

(I)

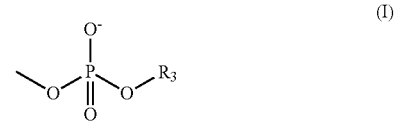

18 Claims, 11 Drawing Sheets

CELL CRYOPRESERVATION PROTECTIVE COMPOSITION AND USE THEREOF

This application is the U.S. National Stage entry under 35 U.S.C. § 371 of PCT/CN2017/079744, filed on Apr. 7, 2017, which claims priority to Chinese Application No. 201610223983.4, filed on Apr. 8, 2016.

TECHNICAL FIELD

The present application belongs to the field of cell biology, and in particular relates to utilizing a cell cryopreservation protective composition which comprises a zwitterionic molecule having a structure of general formula $R_1$—$N^+$ $(CH_3)_2$—$(CH_2)_n$—$R_2$ and is non-toxic and highly efficient. The present application also relates to use of the composition and a method of cryopreserving cells.

BACKGROUND

Along with the development of biomedical technology, living cells extracted from animal bodies are increasingly widely used in various fields of biomedicine. For example, in the field of pharmaceutical development, living cells are used to investigate efficacy, dosage and toxicity of drugs, which provides guidance for animal experimental testing, while also reduces the number of experimental animals being used and lowers risks; on the one hand, in the medical field, living cell samples obtained from human bodies can be used for detection and diagnosis, and on the other hand, cells having therapeutic functions (such as stem cells, immune cells, and blood cells) have been used to conquer many difficult miscellaneous diseases that endanger human health, such as cancers, diabetes, organ damage, etc. However, after leaving the environment of animal bodies, living cells will quickly die under unsuitable conditions. In the cell culture environment (37° C. incubator, $CO_2$, etc.), although living cells can survive, they will continue to proliferate, age, and even become cancerous. Therefore, efficiently long-term preservation of cells is a necessary prerequisite and a constant challenge for the applications of various types of cells. At present, the most effective means of preserving cells is cryopreservation at low temperatures (−80° C. or −196° C.). In such an ultra-low temperature condition, cell metabolism will slow down or even be suspended, so that the goal of long-term preservation can be achieved. However, in the process of freezing and cooling, the formation of ice crystals will cause the cells to suffer fatal mechanical damage and solute damage. Therefore, cryopreservation of cells often requires the addition of a cryoprotectant to reduce the produced intracellular and extracellular ice crystals. Dimethyl sulfoxide (DMSO), yolk and glycerol are currently the most commonly used conventional cryoprotectants, and due to different cell permeability and structures, these cryoprotectants are suitable for different cell types. DMSO is suitable for cryopreservation of animal somatic cells; glycerol is commonly used as a cryoprotectant for bacterial cells, human and livestock germ cells, and blood cells; yolk is commonly used as an auxiliary additive for a cryoprotectant for germ cells. However, all conventional cryoprotectants have their fatal flaws. DMSO has certain cytotoxicity. For example, DMSO inhibits cell proliferation, alters the biological functions of cells, and induces differentiation of stem cells, etc. (for details, see K. Aita et al. "Apoptosis in murine lymphoid organs following intraperitoneal administration of dimethyl sulfoxide (DMSO)", *Experimental and Molecular Pathology*, 2005, 79, 265-271; R. Pal et al. "Diverse effects of dimethyl sulfoxide (DMSO) on the differentiation potential of human embryonic stem cells", *Archives of Toxicology*, 2012, 86, 651-661; B. Hegner et al. "Differential regulation of smooth muscle markers in human bone marrow-derived mesenchymal stem cells", *Journal of Hypertension*, 2005, 23, 1191-1202.). Therefore, if DMSO is used as a cell cryoprotectant, it is necessary to shorten the contact time between DMSO and cells under non-frozen state as far as possible. In addition, before the cells are used, sufficient rinsing is required to remove DMSO. However, there are still a considerable amount of studies showing that in the field of cell therapy, if the stem cells which have been preserved with DMSO are used, no matter how cells are rinsed, the cells will cause fatal side effects on human bodies after they are injected into the human bodies. On the one hand, it may be because the DMSO that has entered the cells can hardly be washed away, and on the other hand, the DMSO may have caused a detrimental effect on the physiological functions and activities of the cells (for details, see B. Calmels et al. "Preclinical evaluation of an automated closed. Fluid management device: Cytomate™, for washing out DMSO from hematopoietic stem cell grafts after thawing". *Bone Marrow Transplantation.* 2003, 31, 823-828.).

Glycerol, as the first discovered conventional cryoprotectant, was successfully used in cryopreservation of rooster sperms. However, the disadvantages of glycerol include that it has poor permeability, that it enters cells very slowly, and that it has no cryopreservation effect on many types of cells; meanwhile, due to the poor permeability of glycerol, cells are susceptible to damages caused by osmotic pressure in the process of removing glycerol, especially at a high concentration of glycerol cryoprotectant (cryoprotectants for blood usually contain 40% glycerol); besides, examples that glycerol affects cell functions have also been reported (for details, see J Witowski et al. "Glycerol toxicity for human peritoneal mesothelial cells in culture: comparison with glucose", *International Journal of Artificial Organs*, 1994, 17(5):252-260). Furthermore, as an auxiliary additive for a cryoprotectant, yolk also has the following deficiencies: 1) yolk has complex components and contains some components harmful to cells, such as large particulate matters, lipoproteins at high concentrations, etc.; 2) yolk usually originates from eggs of poultry, so it may carry some potentially infectious pathogens (viruses, bacteria, and mycoplasma) and increase the risk of disease transmission; 3) the quality of yolk from different sources varies, so there are differences in the effects of cryopreservation and it is difficult to achieve standardization. Therefore, the limitations such as low efficiency and risks of conventional cryoprotectants have become the bottleneck for successful applications of living cells in various fields, especially in clinical fields such as cell therapy, regenerative medicine, and the like.

In addition to the inherent toxicity of conventional cryoprotectants, there is also another deficiency: the cryopreservation procedures using conventional protectants are stepwise cooling, which usually needs about one day. This is because the ability of DMSO or glycerol to enter cells is limited, and in order to make it possible for them to slowly permeate into cells and reduce intracellular mechanical and solute damage caused by ice crystals, stepwise cooling (e.g., at a cooling rate of 1° C. per minute) is required, i.e., it is necessary to mix DMSO- or glycerol-containing cryoprotectants with cells, sequentially place the mixtures under the conditions of 4° C., −20° C., and −80° C. respectively for a certain period of time, and finally transfer the mixtures to a liquid nitrogen tank to meet the requirement of stepwise cooling in conventional cryopreservation procedures. Such stepwise cooling procedures are very cumbersome and time-consuming, which not only prolong the contact time between toxic cryoprotectants and cells, increase the chance of cell damage, but also require many kinds of refrigerating apparatus (such as a −80° C. low temperature refrigerator, a −20° C. refrigerator, a 4° C. refrigerator, a liquid nitrogen tank, etc.); and moreover, once the requirement for cooling rate, namely, "slow freeze" is not satisfied, the cryopreservation efficiency may decrease significantly. Therefore, developing a non-toxic and highly efficient cryoprotectant that does not require cumbersome cryopreservation steps is of great significance in the biomedical field or the like.

Furthermore, Patent Document 1 (U.S. Pat. No. 4,980,277) discloses a composition for transportation and storage of sperms and ova of domestic animals, and the composition comprises 5 mL (87%) of glycerol, a Merk solution, and other components, and the Merk solution contains EDTA. It is known to those skilled in the art that glycerol is the major substance for protecting cryopreserved cells. Patent Document 1 uses 5 mL (87%) of glycerol to preserve animal sperms. On the one hand, it is glycerol that is the cryoprotectant playing a decisive role in cryopreservation of sperms. For details, see reference (Polge et al. "Revival of spermatozoa after vitrification and dehydration at low temperature". *Nature* 164: 666 (1949)). And on the other hand, EDTA has great cytotoxicity. It is well known that EDTA is a $Ca_2^+$ ion chelator that chelates the calcium ions necessary for cells to thus affect cells. Besides, EDTA also has significant toxic effects on human bodies. For example, it can irritate the skin and mucous membranes, and thus cause symptoms such as asthma and skin rash, so it is a substance that may cause allergies. It will cause a series of detrimental effects including calcium deficiency, blood pressure lowering, kidney dysfunction, chromosomal abnormality, and native mutation after it is ingested by human bodies via transdermal absorption aids such as propylene glycol (for details, see Singh K. et al. "Interaction of EDTA with tributyltin induced cellular toxicity". *Indian J Exp Biol.* 1989 September; 27(9): 833-4.).

SUMMARY

Problems to be Solved by the Disclosure

The present disclosure aims to redress the deficiencies of cryoprotectants in the present cell cryopreservation technology, such as high toxicity, cumbersome operation, and unstable efficiency of cryopreservation by providing a cell cryopreservation protective composition, which comprises a zwitterionic molecule having a structure of general formula $R_1$—$N^+(CH_3)_2$—$(CH_2)_n$—$R_2$ and needs no assistance from any cell toxic cell cryopreservation component (e.g., glycerol or DMSO), and by providing use of the composition and a method of cryopreserving cells using the composition. The cell cryopreservation protective composition of the present disclosure can be applied to a wide range of cell concentrations and cell types for cryopreservation, and can achieve a high survival rate after cell recovery. In addition, cryopreservation procedures using the cryopreservation composition provided by the method are simple and easy to carry out, do not need various large-scale cryopreservation apparatus, and can effectively reduce the cell cryopreservation cost and improve cryopreservation efficiency.

Means for Solving the Problems

In a first aspect, the present application provides a cell cryopreservation protective composition comprising one or more zwitterionic molecules having a structure of general formula $R_1$—$N^+(CH_3)_2$—$(CH_2)_n$—$R_2$, and a nutrient ingredient for cells, wherein said zwitterionic molecules are 10 to 2530 parts by mass with respect to 100 parts by mass of said nutrient ingredient for cells;

said cell cryopreservation protective composition excludes the following substances: glycerol, diaminoethane tetraacetic acid or salts thereof, dimethyl sulfoxide, or yolk, and in said structure of general formula $R_1$—$N^+(CH_3)_2$—$(CH_2)_n$—$R_2$, said $R_1$ is linear or branched alkyl having 1 to 10 carbon atoms, and is optionally substituted with a substituent selected from the group consisting of (meth)acryloylamino, (meth)acryloyloxy, alkenyl, hydroxyl, hydroxyalkyl, alkoxyl, and halogen, said $R_2$ is any negatively charged group selected from the group consisting of —COO⁻, —$SO_4^-$, —$SO_3^-$, and

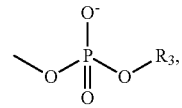

and said $R_3$ is a group selected from the group consisting of (meth)acryloyloxyalkyl, alkyl, and alkenyl, said $(CH_3)_2$ and $(CH_2)_n$ may each independently be optionally substituted with a substituent selected from the group consisting of alkyl, alkenyl, hydroxyl, hydroxyalkyl, alkoxyl, a polyalkylene oxide group, and halogen, and n is an integer from 1 to 10.

In said cell cryopreservation protective composition, in said structure of general formula R $R_1$—$N^+(CH_3)_2$—$(CH_2)_n$—$R_2$, said $R_1$ is linear or branched alkyl having 1 to 5 carbon atoms, and is optionally substituted with a substituent selected from the group consisting of (meth)acryloylamino, (meth)acryloyloxy, hydroxyl, hydroxyalkyl, alkoxyl, and halogen, said $R_2$ is any group selected from the group consisting of —COO⁻, —$SO_3^-$, and

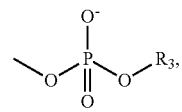

and said $R_3$ is (meth)acryloyloxyalkyl, the hydrogen atoms in said $(CH_3)_2$ and $(CH_2)_n$ may each independently be optionally substituted with a substituent selected from the group consisting of alkyl, hydroxyl, hydroxyalkyl, alkoxyl, a polyalkylene oxide group, and halogen, and n is an integer from 1 to 5.

In said cell cryopreservation protective composition, said zwitterionic molecules are 420 to 1120 parts by mass with respect to 100 parts by mass of said nutrient ingredient for cells; and in said structure of general formula $R_1$—$N^+(CH_3)_2$—$(CH_2)_n$—$R_2$, said $R_1$ is linear or branched alkyl having 1 to 3 carbon atoms, and is optionally substituted with a substituent selected from the group consisting of (meth)acryloylamino, (meth)acryloyloxy, hydroxyl, hydroxyalkyl having 1 to 5 carbon atoms, and alkoxyl having 1 to 5 carbon atoms, the hydrogen atoms in said $(CH_3)_2$ and $(CH_2)_n$ may each independently be optionally substituted with a substituent selected from the group consisting of alkyl having 1 to 5 carbon atoms, hydroxyl, hydroxyalkyl having 1 to 5 carbon atoms, alkoxyl having 1 to 5 carbon atoms, and a polyalkylene oxide group, and n is an integer from 1 to 3.

In said cell cryopreservation protective composition, 100 parts by mass of said nutrient ingredient for cells comprise components of the following parts by mass:

| | |
|---|---|
| one or more amino acids | 5 to 15 parts; |
| one or more salts | 45 to 75 parts; |
| one or more saccharides | 8 to 32 parts; |
| one or more vitamins | 0.1 to 1.0 part; and |
| one or more proteins | 0.5 to 10 parts. |

In said cell cryopreservation protective composition, said zwitterionic molecule having the structure of general formula $R_1$—$N^+(CH_3)_2$—$(CH_2)_n$—$R_2$ is $CH_3$—$N^+(CH_3)_2$—$CH_2$—$COO^-$.

In said cell cryopreservation protective composition, in the zwitterionic molecule having the structure of general formula $R_1$—$N^+(CH_3)_2$—$(CH_2)_n$—$R_2$, the hydrogen atom in $(CH_2)_n$ is substituted with hydroxyl and $R_2$ is —$COO^-$.

In said cell cryopreservation protective composition, said cell cryopreservation protective composition is used for protecting human cells or animal cells during cryopreservation; and preferably used for protecting human cells or mammalian cells.

In said cell cryopreservation protective composition, said human cells or mammalian cells comprise at least one of cancer cells, somatic cells, and stem cells; and preferably the somatic cells are immune cells or blood cells.

In said cell cryopreservation protective composition, said cell cryopreservation protective composition is used for protecting human cells during cryopreservation; preferably said human cells comprise at least one of lung cancer cells, cervical cancer cells, mammary gland cells, hematopoietic stem cells, immune cells, umbilical cord mesenchymal stem cells, bone marrow mesenchymal stem cells, lymphatic cancer cells, and blood cells.

In said cell cryopreservation protective composition, said nutrient ingredient for cells is one or more salts; and preferably said salts comprise inorganic salts; and it is also preferable that the inorganic salts are present in the form of physiological saline or buffer; it is further preferable that said buffer is phosphate buffer.

In a second aspect, the present application provides a cell cryopreservation protective solution, which is an aqueous solution of the above cell cryopreservation protective composition, wherein the content of the zwitterionic molecules in the cell cryopreservation protective solution is 0.1 to 20 mass %, based on the total mass of the cell cryopreservation protective solution.

In said cell cryopreservation protective solution, the content of the zwitterionic molecules in the cell cryopreservation protective solution is 4 to 10 mass %, based on the total mass of the cell cryopreservation protective solution.

In a third aspect, the present application provides a method of cryopreserving cells, comprising: suspending cells in the above cell cryopreservation protective solution, placing the solution in a cryopreservation container, and then performing cryopreservation.

In said method of cryopreserving cells, said cryopreservation is ultrarapid cryopreservation.

In said method of cryopreserving cells, after said cryopreservation is performed, the cryopreserved cells are recovered, and then said cells are directly used or used in a diluted manner.

In said method of cryopreserving cells, the recovery survival rate of said cells is at least 70%; and preferably the recovery survival rate of said cells is 80% to 99%.

In said method of cryopreserving cells, cells are suspended in said cell cryopreservation protective solution at such a concentration that $1 \times 10^4$ to $1 \times 10^9$ cells are suspended in 1.0 mL to 5.0 mL of said cell cryopreservation protective solution; and it is preferable that cells are suspended in said cell cryopreservation protective solution at such a concentration that $1 \times 10^5$ to $1 \times 10^7$ cells are suspended in 1.5 mL to 1.8 mL of said cell cryopreservation protective solution.

In said method of cryopreserving cells, the temperature range of cryopreservation is $-20°$ C. to $-196°$ C.; and preferably $-80°$ C. to $-196°$ C.

In a fourth aspect, the present application provides use of the above cell cryopreservation protective composition in cell cryopreservation, said cells being human cells or animal cells; and preferably said cells being human cells or mammalian cells.

In said use, said human cells or mammalian cells comprise at least one of cancer cells, somatic cells, and stem cells; and preferably the somatic cells are immune cells or blood cells.

In said use, said cells are human cells; preferably said human cells comprise at least one of lung cancer cells, cervical cancer cells, mammary gland cells, hematopoietic stem cells, immune cells, umbilical cord mesenchymal stem cells, bone marrow mesenchymal stem cells, lymphatic cancer cells, and blood cells.

Advantageous Effects

In order to redress the deficiencies in the present technology of cryopreserving cells, the present disclosure provides a cell cryopreservation protective composition which is non-toxic and highly efficient, can be used in a simple cryopreservation method, and can enable the cells to be directly used without washing after cell recovery, and provides a method using the composition for performing cryopreservation. The cryopreservation composition comprising the zwitterionic molecule having the structure of general formula $R_1$—$N^+(CH_3)_2$—$(CH_2)_n$—$R_2$ has not yet been reported. Therefore, the cell cryopreservation protective composition provided by the present application is imperative in respect of practical significance and application value, and has a revolutionary promoting effect on scientific research, biomedicine, clinical treatment and other fields.

The technical effects of the present disclosure are summarized as follows:

1) The cell cryopreservation protective composition provided by the present disclosure can play a protective role in the cell cryopreservation process, and can achieve an extremely high recovery cell survival rate, because the components of the composition include a zwitterionic molecule having a structure of general formula $R_1$—$N^+(CH_3)_2$—$(CH_2)_n$—$R_2$, which has the function of regulating cell osmotic pressure or lowering the freezing point.

2) The cell cryopreservation protective composition provided by the present disclosure is used with simple and easy-to-conduct cryopreservation steps, and is preferably directly placed in a cryopreservation container in a cryopreservation device (including liquid nitrogen or cryogenic refrigerator) to perform ultrarapid cryopreservation without stepwise cryopreservation, so that the low survival rate after cell recovery caused by instability of cooling rate in conventional "slow freeze" storage technology is avoided, and the number of cryopreservation devices to be used is greatly reduced.

3) The effective ingredient of the cell cryopreservation protective composition provided by the present disclosure is a zwitterionic molecule having a structure of general formula $R_1—N^+(CH_3)_2—(CH_2)_n—R_2$, and the cell cryopreservation protective composition of the present disclosure excludes the following substances: glycerol, diaminoethane tetraacetic acid or salts thereof, dimethyl sulfoxide, or yolk, so unlike conventional cryoprotectants, it is completely harmless to cells. The zwitterionic molecules having the structure of general formula $R_1—N^+(CH_3)_2—(CH_2)_n—R_2$, according to the present disclosure include compounds isolated from natural substances, compounds modified or derivatized based on natural compounds, and synthetic compounds satisfying the structure of general formula described above, and the compounds themselves are not toxic to cells. Therefore, it is not necessary to repetitively rinse the cells after recovery so as to remove toxic cryoprotectant, which brings a broad application prospect in the medical clinical fields, especially in the fields such as cell therapy and the like.

LIST OF REFERENCE SIGNS

1. A cell
2. An ice crystal
3. A cell cryoprotectant

DETAILED DESCRIPTION

The technical solutions of the present disclosure will be further described in detail with reference to the following Examples, but the present disclosure is not limited by these specific Examples.

Figure 1A:
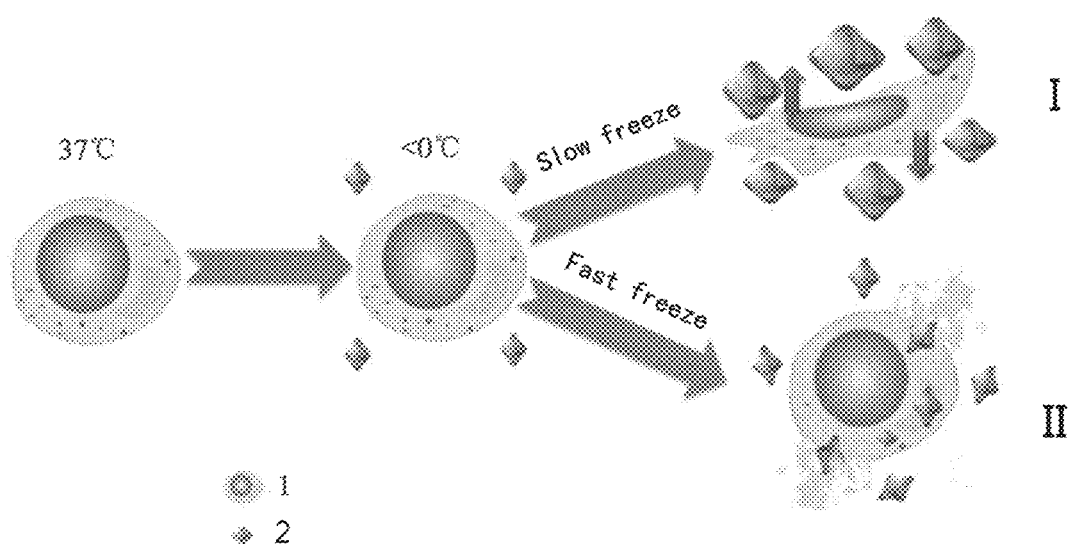
FIG. 1a: a schematic diagram of the principle of cryodamage during conventional low-temperature cryopreservation.

As shown in FIG. 1a, during low-temperature cryopreservation, cells are often subjected to cryodamage which causes death of the cells. In 1970, Mazur proposed the hypothesis of two factors of cryodamage, as shown in FIG. 1a. When the temperature of a cell 1 falls below the freezing point, if the cooling rate is too slow, an extracellular ice crystal 2 is formed earlier than an intracellular ice crystal, which causes the extracellular osmotic pressure to rise suddenly, and due to the difference in osmotic pressure between the inside and the outside of the cell, a large amount of the intracellular flowing water will permeate out of the cell through cell membrane, leading to cell dehydration and death—this is known as solute damage (I); if the cooling rate is too fast, the water inside the cell does not have enough time to permeate out of the cell before it freezes inside the cell, and the formed ice crystals can cause fatal damage to the organelles, proteins, and membrane structures inside the cell—this is mechanical damage (II).

Figure 1B:
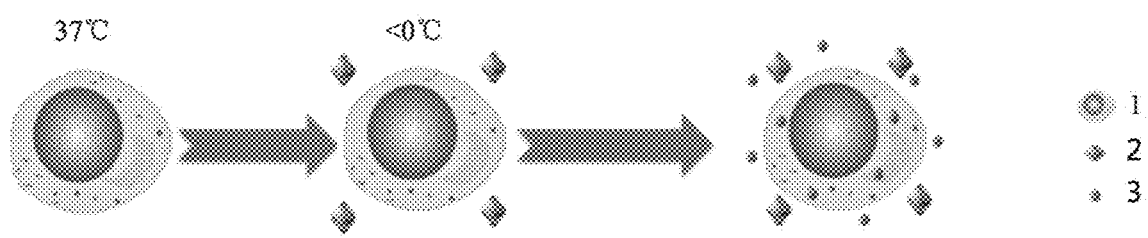
FIG. 1b: a schematic diagram of the principle of cell protection by the cell cryopreservation protective composition provided by the present disclosure during conventional low-temperature cryopreservation.

As shown in FIG. 1b, a cell cryoprotectant 3 (specifically, a zwitterionic molecule) contained in a cell cryopreservation protective composition provided by the present disclosure has functions such as regulating osmotic pressure, moderating a stress response, reducing the freezing point of water, protecting proteins, and the like, and it plays a decisive role in avoiding the two kinds of cryodamage in cell cryopreservation, thereby protecting the cell and guaranteeing the survival of the cell.

The cell cryopreservation protective composition of the present application comprises a cell cryoprotectant and a nutrient ingredient for cells, wherein the cell cryoprotectant comprises one or more zwitterionic molecules having a structure of general formula $R_1—N^+(CH_3)_2—(CH_2)_n—R_2$. For example, the cell cryoprotectant in the cell cryopreservation protective composition of the present application is the above-mentioned zwitterionic molecules, or a combination of the above-mentioned zwitterionic molecules and other conventional cryoprotectants.

In the cell cryopreservation protective composition of the present application, the above zwitterionic molecules are comprised in an amount of 10 to 2530 parts by mass with respect to 100 parts by mass of the nutrient ingredient for cells, and the cell cryopreservation protective composition excludes harmful substances, for example, substances that are harmful to cells, which are exemplified by glycerol, diaminoethane tetraacetic acid or salts thereof, dimethyl sulfoxide, or yolk.

In the cell cryopreservation protective composition of the present application, the above amphoteric molecules are preferably comprised in an amount of 420 to 1120 parts by mass with respect to 100 parts by mass of the nutrient ingredient for cells.

In the structure of general formula $R_1$—$N^+(CH_3)_2$—$(CH_2)_n$—$R_2$, the nitrogen atom is positively charged and $R_2$ is a negatively charged group. Wherein, $R_1$ described above is linear or branched alkyl having 1 to 10 carbon atoms, and is optionally substituted with a substituent selected from the group consisting of (meth)acryloylamino, (meth)acryloyloxy, alkenyl, hydroxyl, hydroxyalkyl, alkoxyl, and halogen. The word "substituted" means that the hydrogen atom in the group is substituted with a substituent.

$R_2$ is any negatively charged group selected from the group consisting of —COO⁻, —SO₄⁻, —SO₃⁻, and

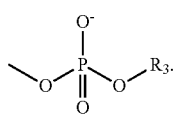

$R_3$ is a group selected from the group consisting of (meth)acryloyloxyalkyl, alkyl and alkenyl.

The $(CH_3)_2$ and $(CH_2)_n$ may each independently be optionally substituted with a substituent selected from the group consisting of alkyl, alkenyl, hydroxyl, hydroxyalkyl, alkoxyl, a polyalkylene oxide group, and halogen, and n is an integer from 1 to 10.

The zwitterionic molecules having the structure of general formula $R_1$—$N^+(CH_3)_2$—$(CH_2)_n$—$R_2$ belong to nitrogen- and oxygen-containing zwitterionic molecules, and the structure of general formula may have various substituents. The cell cryopreservation protective composition of the present application comprises zwitterionic molecules having a structure of general formula $R_1$—$N^+(CH_3)_2$—$(CH_2)_n$—$R_2$ and excludes harmful components such as glycerol, diaminoethane tetraacetic acid or salts thereof, dimethyl sulfoxide, or yolk.

The zwitterionic molecules having the structure of general formula $R_1$—$N^+(CH_3)_2$—$(CH_2)_n$—$R_2$ include compounds isolated from natural substances, compounds modified or derivatized based on natural compounds, and synthetic compounds satisfying the structure of general formula described above. Naturally occurring zwitterionic molecules include $CH_3$—$N^+(CH_3)_2$—$CH_2$—COO (which compound is sometimes called "betaine" or "natural betaine" for short), phosphorylcholine derivatives, L-carnitine and the like extracted from natural substances.

The zwitterionic molecules having such the structure of general formula are preferably betaine based compounds. The betaine based compounds include all compounds having the structure of $R_1$—$N^+(CH_3)_2$—$(CH_2)_n$—COO and extend to similar compounds containing sulfur and phosphorus in anions. Wherein, in the linking group $(CH_2)_n$ between cation and anion, n is an integer from 1 to 10, and $(CH_2)_n$ may each independently be optionally substituted with a substituent selected from the group consisting of alkyl, alkenyl, hydroxyl, hydroxyalkyl, alkoxyl, a polyalkylene oxide group, and halogen. $R_1$ is as defined above.

Among the betaine based compounds, betaine and its derivatives, phosphorylcholine derivatives, and L-carnitine are preferably used. The structure of betaine can be represented as

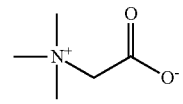

(i.e., $CH_3$—$N^+(CH_3)_2$—$CH_2$—COO⁻, which is also referred to as trimethylammonium acetate, or Oxyneurine). Betaine derivatives are preferably sulfobetaine, carboxybetaine (meth)acryloylamide, carboxybetaine alkyl (meth)acrylate, and the like. Betaine can be extracted from a variety of microorganisms, plants and animals and is an important component of many foods such as wheat, spinach, beet, shellfish and fish. It is reported that the daily safe intake of betaine by an adult is 9 g to 15 g, and the concentration of betaine in the blood can reach 20 to 70 µmol/L. In addition to natural betaine, synthetic betaine is also suitable for use in the present disclosure.

The zwitterionic molecules having the structure of general formula $R_1$—$N^+(CH_3)_2$—$(CH_2)_n$—$R_2$ have the functions of rapidly regulating osmotic pressure of cells in vivo and moderating a stress response, and can also play a protective role for intracellular proteins (e.g., enzymes). They have good biocompatibility and are easily and quickly absorbed by cells, and they have been widely used in many medicine fields such as anti-tumor, anti-fatty liver, and ulcer treatment, and in the field of skin care products.

In the zwitterionic molecules having the structure of general formula $R_1$—$N^+(CH_3)_2$—$(CH_2)_n$—$R_2$, $R_2$, it is preferred that the above $R_2$ is any group selected from the group consisting of —COO⁻, —SO₃⁻, and

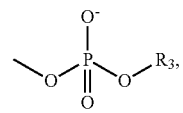

and the $R_3$ is (meth)acryloyloxyalkyl. It is also preferred that the hydrogen atom in $(CH_2)_n$ is substituted with hydroxyl and $R_2$ is —COO⁻.

Among all the zwitterionic molecules having the structure of general formula $R_1$—$N^+(CH_3)_2$—$(CH_2)_n$—$R_2$, $CH_3$—$N^+(CH_3)_2$—$CH_2$—COO⁻ is most preferred.

In the case where $R_2$ in the zwitterionic molecules having the structure of general formula $R_1$—$N^+(CH_3)_2$—$(CH_2)_n$—$R_2$ is COO⁻, the zwitterionic molecules having the structure of general formula $R_1$—$N^+(CH_3)_2$—$(CH_2)_n$—$R_2$ may also be carboxybetaine (meth)acrylamide in which $R_1$ is (meth)acryloylamino, and/or carboxybetaine alkyl (meth)acrylate in which $R_1$ is a alkyl (meth)acrylate group.

In a specific technical solution, as the zwitterionic molecule having a structure of general formula $R_1$—$N^+$$(CH_3)_2$—$(CH_2)_n$—$R_2$, betaine (Compound 1); (3-acryloylaminopropyl)-(2-carboxyethyl)-dimethylammonium having the structure of (Compound 2)

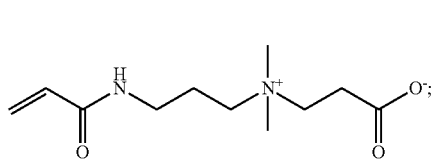

3-((2-(methacryloyloxy)ethyl) dimethylammonio) propanoate having the structure of

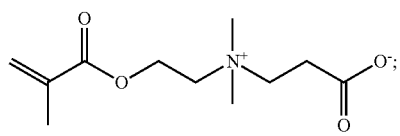

(Compound 3)

3-[dimethyl-[2-(2-methylprop-2-enoyloxy)ethyl]azaniumyl]propane-1-sulfonate having the structure of

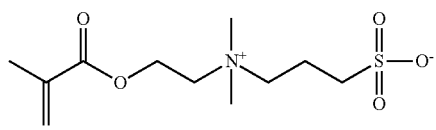

(Compound 4)

(hereinafter sometimes referred to as "sulfobetaine" for short); 2-(methacryloyloxy)ethyl-2-(trimethylammonio) ethyl phosphate having the structure of

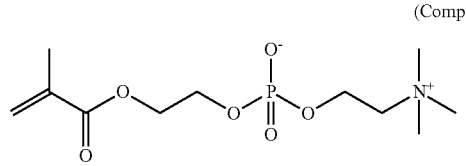

(Compound 5)

(hereinafter sometimes referred to as "phosphorylcholine derivatives" for short); or, 3-carboxy-2-hydroxy-N,N,N-trimethyl-1-propanaminium inner salt (2R) having the structure of

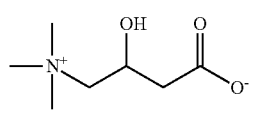

(Compound 6)

(hereinafter sometimes referred to as "L-carnitine") can be used. Wherein, each group which is not explicitly shown in each structural formula representing Compounds 1 to 6 in this paragraph is carbon atom(s) and hydrogen atom(s) connected thereto, such as $CH_3$, $CH_2$, CH, and C.

It should be noted that among the various groups used in the present application whose number of carbon atoms are not limited (the groups include but are not limited to alkyl, alkenyl, hydroxyl, hydroxyalkyl, alkoxyl, a polyalkylene oxide group), each group has 1 to 20 carbon atoms, more preferably 1 to 10 carbon atoms, further preferably 1 to 5 carbon atoms, still preferably 1 to 3 carbon atoms, and most preferably 1 or 2 carbon atoms. Among them, the polyalkylene oxide group has 4 to 20 carbon atoms, more preferably 4 to 10 carbon atoms; the polyalkylene oxide group is more preferably a polyethylene oxide group (i.e., a polyoxyethylene group). It is also preferred that the two methyl groups linked to $N^+$ in the structure of general formula $R_1-N^+(CH_3)_2-(CH_2)_n-R_2$ are all or partially substituted with a polyoxyethylene group or hydroxyethyl. In addition, the (meth)acryloyloxyalkyl in $R_3$ is preferably (meth)acryloyloxy-substituted linear or branched alkyl having 1 to 10 carbon atoms, more preferably (meth)acryloyloxy-substituted linear or branched alkyl having 1 to 5 carbon atoms, and most preferably (meth)acryloyloxy-substituted methyl or ethyl.

In the present disclosure, the nutrient ingredient for cells is a substance conventionally used for culturing cells in the field of cell culture medium, and the substance has, for example, a function of supplying nutrients to cells and/or a function of promoting reproduction and proliferation of cells. The nutrient ingredient for cells is preferably at least one substance selected from the group consisting of the following substances: one or more amino acids, one or more salts, one or more saccharides, one or more vitamins, and one or more proteins. The nutrient ingredient for cells more preferably comprises one or more amino acids, one or more salts, one or more saccharides, one or more vitamins, and one or more proteins.

In the present disclosure, the specific components in the nutrient ingredient for cells, such as amino acids, salts, saccharides, vitamins, proteins, and the like, may be the same as the corresponding common components in cell culture mediums. The amino acids may be the 20 common natural amino acids, for example, natural amino acids including at least one of arginine, glycine, leucine, glutamic acid, isoleucine, and glutamine; the salts can regulate the osmotic pressure of the extracellular environment and provide the necessary salts for cells, and the salts are preferably inorganic salts, which may include at least one of NaCl, $NaHCO_3$, KCl, $Ca(NO_3)_2$, $MgSO_4$, and $KH_2PO_4$; the saccharides can provide necessary protection for cells, regulate osmotic pressure, and provide a suitable environment for cells, etc., and the saccharides may include at least one of glucose and sucrose; the vitamins include vitamin B1, vitamin B6, biotin, and calcium D-pantothenate, folic acid, i-inositol, nicotinamide, choline chloride, pyridoxol hydrochloride, riboflavin, thiamine hydrochloride, and vitamin B12; and/or, the proteins include at least one of albumin and serum (which contains albumin).

In the present disclosure, the specific component content in the nutrient ingredient for cells, such as amino acid content, salt content, saccharide conent, vitamin content, protein content, and the like, may be the same as the contents of the corresponding common components in cell culture mediums. For example, 100 parts by mass of the nutrient ingredient for cells comprise components the following in terms of parts by mass: 5 to 15 parts of one or more amino acids; 45 to 75 parts of one or more salts; 8 to 32 parts of one or more saccharides; 0.1 to 1.0 parts of one or more vitamins; and 0.5 to 10 parts of one or more proteins. Preferably, 100 parts by mass of the nutrient ingredient for cells comprise components of the following parts by mass: 9 to 14 parts of one or more amino acids; 50 to 73 parts of one or more salts; 9 to 24 parts of one or more saccharides; 0.1 to 0.5 parts of one or more vitamins; and 0.9 to 9 parts of one or more proteins. In the present disclosure, the nutrient ingredient for cells is preferably constituted as such that the aqueous solution obtained after dissolving the nutrient ingredient for cells in water is maintained within the range of the cell osmotic pressure. For example, the pH of the aqueous solution is preferably about 7.4.

When the cell cryopreservation protective composition of the present disclosure is used, an aqueous solution, obtained by mixing all components (the zwitterionic molecules and the nutrient ingredient for cells) of the composition and then dissolving them in an appropriate amount of water, can be used as the cell cryopreservation protective solution. Alternatively, an aqueous solution, obtained by firstly dissolving a portion of the components (e.g., the nutrient ingredient for cells) of the composition in water, and then adding the remaining components (e.g., the zwitterionic molecules) of the composition into the aqueous solution, can be used as the cell cryopreservation protective solution. The cell cryopreservation protective solution of the present application can be obtained by either one of the above two manners of operation.

There is no particular limitation on the amount of the water used in the preparation of the cell cryopreservation protective solution of the present application, and any conventional amount in the art can be used. Among them, the content of the zwitterionic molecules in the cell cryopreservation protective solution is preferably 0.1 to 20 mass %, and further preferably the content of the zwitterionic molecules is 4 to 10 mass %, based on the total mass of the cell cryopreservation protective solution.

After the above-described cell cryopreservation protective solution is prepared, it is preferable to further adjust the pH to be approximately neutral, for example, adjusting the pH of the cryopreservation protective solution to 7.2 with an appropriate amount of HCFNaOH. In addition, it is also preferable to further filter and sterilize the treated cell cryopreservation protective solution, for example, filtering and sterilizing it with a 0.22 μm disposable sterile filter membrane. The major steps of cryopreserving cells using the cryopreservation protective composition provided by the present disclosure are as follows: (1) preparing a cell cryopreservation protective solution containing a cell cryopreservation protective composition comprising zwitterionic molecules having a structure of general formula $R_1$—$N^+$ $(CH_3)_2$—$(CH_2)_n$—$R_2$; (2) suspending a certain number of cells in the cell cryopreservation protective solution and placing the solution in a cryopreservation container to perform cryopreservation, and preferably performing cryopreservation by means of directly immersing the container in a cryopreservation device (a conventional cryopreservation device in the art, such as liquid nitrogen or a cryogenic refrigerator, etc.); (3) after the cells are recovered, taking the cryopreservation container out of the cryopreservation device, thawing and recovering the cells, and thereafter directly using the cells or using them after they are slightly diluted (for example, in cell therapy, the cells can be directly injected into a patient's body).

The cryopreservation protective composition and the cell cryopreservation protective solution containing the composition provided by the present disclosure are used for protecting human cells or animal cells during cryopreservation; preferably for protecting human cells or mammalian cells. Wherein the human cells or mammalian cells preferably comprise at least one of cancer cells, somatic cells, and stem cells; and more preferably the somatic cells are immune cells or blood cells.

Wherein, the stem cells include cells such as hematopoietic stem cells, embryonic stem cells, pluripotent stem cells, and the like. The somatic cells are human or animal cells other than non-differentiated stem cells, cancer cells, and germ cells; and wherein the immune cells include cells such as T cells, macrophages, and the like.

Furthermore, the cell cryopreservation protective composition and the cell cryopreservation protective solution containing the composition are preferably used for protecting human cells during cryopreservation; and more preferably, the human cells comprise at least one of lung cancer cells, cervical cancer cells, mammary gland cells, hematopoietic stem cells, immune cells, umbilical cord mesenchymal stem cells, bone marrow mesenchymal stem cells, lymphatic cancer cells, and blood cells.

Preparation Examples

Unless otherwise specified, the reagents, raw materials, cells and the like used in Preparation Examples and Effect Examples of the present application are all commercially available or can be prepared by conventional methods in the art.

Source of Material

Betaine (from Beijing InnoChem Science & Technology Co., LTD. Acros, Item No. 204241000)-Compound 1;

Sulfobetaine (from Tianjin Heowns Biochemical Technology Co., Ltd., Item No. M-58510)-Compound 4;

Phosphorylcholine derivatives (from Tianjin Heowns Biochemical Technology Co., Ltd., Item No. P-013898)-Compound 5;

L-carnitine (from Dalian Meilun Biotechnology Co., LTD., Item No. MB3278)-Compound 6.

(3-Acryloylaminopropyl)-(2-carboxyethyl)-dimethylammonium (Compound 2), which was prepared by the following method: the system was purged with nitrogen for 15 min using a 500 mL three-neck flask, and air and water vapor therein were removed; 300 mL of anhydrous acetone and 53.98 g of dimethylaminoethyl methacrylate were added, and the mixture was stirred at room temperature for half an hour until the solid was completely dissolved; the mixture was protected with nitrogen, and then 25 g of β-propiolactone was added dropwise; the reaction lasted for 2 h and filtration began; the product was washed with diethyl ether every 15 to 30 min, and after all the product was collected, the product was placed in a round-bottomed flask; then the flask was vacuumed for 1.5 h (diaphragm pump), re-vacuumed for 1 to 2 h (vacuum pump with cold trap), and the product was dissolved in methanol (1:1 w/w); triethylamine was added to the solution until the solution became turbid; methanol was added to clarify the solution and the solution was stirred for 5 h; then anhydrous acetone was added dropwise, a solid was precipitated, and the solution was allowed to stand still for 30 min; a monomer was obtained until the solid was fully precipitated. The structure of the compound as determined by nuclear magnetic resonance spectroscopy detection is (3-acryloylaminopropyl)-(2-carboxyethyl)-dimethylammonium, and specifically, it was shown in the nuclear magnetic resonance spectroscopy that a compound having carboxyl and acryloylamino was obtained.

3-((2-(Methacryloyloxy)ethyl) dimethylammonio) propanoate (Compound 3), which was prepared by the following method: 156 g of dimethylamino propyl acrylamide was added into a two-neck flask, then 200 mL of methanol was added, and the mixed system was cooled with an ice bath; 60 g of acetic acid was added dropwise to the cooled system, and then 72.06 g of acrylic acid was added; the two-neck flask was wrapped with aluminum foil to be subjected to dark treatment and the solution is stirred for 48 h at room temperature; 250 mL of triethylamine was added dropwise and slowly (for about 15 min); after the solution is stirred for 50 min, 1200 mL of an acetone/triethylamine (molar ratio 1/1) mixture was added dropwise and slowly (for 40 to 50 min) to precipitate carboxybetaine methacrylic acid; after being stirred for 20 min, the solution was filtered, and the filter cake was washed with 500 mL of acetone for three times and vacuum dried to obtain 133 g of carboxybetaine methacrylic acid; the solid obtained in the previous step was dissolved in 266 mL of methanol, 100 mL of triethylamine was added thereto, and the mixed solution was stirred and mixed for 1 h; 1000 mL of the acetone/triethylamine (molar ratio 1/1) mixture was slowly added (for 40 to 50 min) to give 130 g of the product. The structure of the compound as determined by a nuclear magnetic resonance spectroscopy detection is 3-((2-(methacryloyloxy)ethyl) dimethylammonio)propanoate, and specifically, it was shown in the nuclear magnetic resonance spectroscopy that a compound having carboxyl and a methylacrylate group was obtained.

Table 1 below lists corresponding parts by mass of respective components (the zwitterionic molecules and the nutrient ingredients for cells) of the cell cryopreservation protective compositions contained in the obtained cell cryopreservation protective solutions having respective zwitterionic molecule concentrations.

Among them, the operation of preparing the cell cryopreservation protective solutions in Preparation Examples 1 to 21 was carried out as follows: dissolving the nutrient ingredients for cells of the parts by mass as shown in Table 1 into water, and then adding the zwitterionic molecules of the parts by mass as shown in Table 1 to give cell cryopreservation protective solutions having respective zwitterionic molecule concentrations. The operation of preparing the cell cryopreservation protective solutions in Preparation Examples 22 to 39 was carried out as follows: mixing respective components (zwitterionic molecules and nutrient ingredients for cells) of the parts by mass as shown in Table 1 to obtain cell cryopreservation protective compositions and dissolving the cell cryopreservation protective compositions in water to give cell cryopreservation protective solutions having respective zwitterionic molecule concentrations.

TABLE 1

| Component | Preparation Example 1 | Preparation Example 2 | Preparation Example 3 | Preparation Example 4 | Preparation Example 5 | Preparation Example 6 | Preparation Example 7 | Preparation Example 8 | Preparation Example 9 |
|---|---|---|---|---|---|---|---|---|---|
| Parts by mass of zwitterionic molecule (Compound 1) | 4.2 | 25.3 | 11.2 | 0.1 | 6.4 | 17.8 | 2.0 | 1.0 | 8.8 |
| Total parts by mass of nutrient ingredients for cells | 1.0 | 1.0 | 1.0 | 1.0 | 1.0 | 1.0 | 1.0 | 1.0 | 1.0 |
| Composition of nutrient ingredient for cells (No.) | 1 | 2 | 3 | 4 | 5 | 1 | 2 | 3 | 4 |
| Concentration of zwitterionic molecule (Compound 1) (mass %) | 4 | 20 | 10 | 0.1 | 6 | 15 | 2 | 1 | 8 |

| Component | Preparation Example 10 | Preparation Example 11 | Preparation Example 12 | Preparation Example 13 | Preparation Example 14 | Preparation Example 15 |
|---|---|---|---|---|---|---|
| Parts by mass of zwitterionic molecule (Compound 1) | 0 | 11.2 | 0 | 0 | 0 | 5.3 |
| Parts by mass of zwitterionic molecule (Compound 2) | 4.2 | 11.2 | 11.2 | 0.1 | 11.2 | 11.2 |
| Total parts by mass of nutrient ingredients for cells | 1.0 | 1.0 | 1.0 | 1.0 | 1.0 | 1.0 |
| Composition of nutrient ingredient for cells (No.) | 5 | 1 | 2 | 3 | 4 | 5 |
| Total concentration of zwitterionic molecules (mass %) | 4 | 20 | 10 | 0.1 | 10 | 15 |

TABLE 1-continued

| Component | Preparation Example 16 | Preparation Example 17 | Preparation Example 18 | Preparation Example 19 | Preparation Example 20 | Preparation Example 21 |
|---|---|---|---|---|---|---|
| Parts by mass of zwitterionic molecule (Compound 1) | 0 | 0 | 0 | 0.1 | 1.0 | 5.3 |
| Parts by mass of zwitterionic molecule (Compound 2) | 0 | 11.2 | 5.3 | 0 | 1.0 | 5.3 |
| Parts by mass of zwitterionic molecule (Compound 3) | 4.2 | 11.2 | 5.3 | 0.1 | 8.8 | 5.3 |
| Total parts by mass of nutrient ingredients for cells | 1.0 | 1.0 | 1.0 | 1.0 | 1.0 | 1.0 |
| Composition of nutrient ingredient for cells (No.) | 1 | 2 | 3 | 4 | 5 | 1 |
| Total concentration of zwitterionic molecules (mass %) | 4 | 20 | 10 | 0.2 | 10 | 15 |

| Component | Preparation Example 22 | Preparation Example 23 | Preparation Example 24 | Preparation Example 25 | Preparation Example 26 | Preparation Example 27 |
|---|---|---|---|---|---|---|
| Parts by mass of zwitterionic molecule (Compound 4) | 4.2 | 25.3 | 5.3 | 0.1 | 11.2 | 11.2 |
| Parts by mass of zwitterionic molecule (Compound 2) | 0 | 0 | 5.3 | 0 | 0 | 5.3 |
| Total parts by mass of nutrient ingredients for cells | 1.0 | 1.0 | 1.0 | 1.0 | 1.0 | 1.0 |
| Composition of nutrient ingredient for cells (No.) | 2 | 3 | 4 | 5 | 1 | 2 |
| Total concentration of zwitterionic molecules (mass %) | 4 | 20 | 10 | 0.1 | 10 | 15 |

| Component | Preparation Example 28 | Preparation Example 29 | Preparation Example 30 | Preparation Example 31 | Preparation Example 32 | Preparation Example 33 |
|---|---|---|---|---|---|---|
| Parts by mass of zwitterionic molecule (Compound 5) | 4.2 | 25.3 | 5.3 | 0.1 | 11.2 | 11.2 |
| Parts by mass of zwitterionic molecule (Compound 3) | 0 | 0 | 5.3 | 0 | 0 | 5.3 |
| Total parts by mass of nutrient ingredients for cells | 1.0 | 1.0 | 1.0 | 1.0 | 1.0 | 1.0 |
| Composition of nutrient ingredient for cells (No.) | 3 | 4 | 5 | 1 | 2 | 3 |

TABLE 1-continued

| Component | Preparation Example 34 | Preparation Example 35 | Preparation Example 36 | Preparation Example 37 | Preparation Example 38 | Preparation Example 39 |
|---|---|---|---|---|---|---|
| Total concentration of zwitterionic molecules (mass %) | 4 | 20 | 10 | 0.1 | 10 | 15 |

| Component | Preparation Example 34 | Preparation Example 35 | Preparation Example 36 | Preparation Example 37 | Preparation Example 38 | Preparation Example 39 |
|---|---|---|---|---|---|---|
| Parts by mass of zwitterionic molecule (Compound 6) | 4.2 | 25.3 | 5.3 | 0.1 | 11.2 | 11.2 |
| Parts by mass of zwitterionic molecule (Compound 5) | 0 | 0 | 5.3 | 0 | 0 | 5.3 |
| Total parts by mass of nutrient ingredients for cells | 1.0 | 1.0 | 1.0 | 1.0 | 1.0 | 1.0 |
| Composition of nutrient ingredient for cells (No.) | 4 | 5 | 1 | 2 | 3 | 4 |
| Total concentration of zwitterionic molecules (mass %) | 4 | 20 | 10 | 0.1 | 10 | 15 |

Wherein, the nutrient ingredients for cells used in respective Preparation Examples consist of respective components in their corresponding masses (mg) as shown in respective compositions of nutrient ingredients for cells No. 1 to No. 5 in the following tables:

Composition of nutrient ingredient for cells No. 1

| No. | Name of compound | Content (mg) |
|---|---|---|
| 1 | L-arginine | 27.74 |
| 2 | L-asparagine | 4.78 |
| 3 | L-aspartic Acid | 1.91 |
| 4 | L-cystine dihydrochloride | 6.23 |
| 5 | L-glutamic acid | 1.91 |
| 6 | Glycine | 0.96 |
| 7 | L-histidine | 1.43 |
| 8 | L-hydroxyproline | 1.91 |
| 9 | L-isoleucine | 4.78 |
| 10 | L-leucine | 4.78 |
| 11 | L-lysine hydrochloride | 3.83 |
| 12 | L-methionine | 1.43 |
| 13 | L-phenylalanine | 1.43 |
| 14 | L-proline | 1.91 |
| 15 | L-serine | 2.87 |
| 16 | L-threonine | 1.91 |
| 17 | L-tryptophan | 0.48 |
| 18 | L-tyrosine | 2.22 |
| 19 | L-valine | 1.91 |
| 20 | P-aminobenzoic acid | 0.10 |
| 21 | Calcium nitrate | 9.57 |
| 22 | Anhydrous magnesium sulfate | 4.67 |
| 23 | Anhydrous sodium dihydrogen phosphate | 64.68 |
| 24 | Potassium chloride | 38.27 |
| 25 | Sodium chloride | 574.00 |
| 26 | Glucose | 191.33 |
| 27 | Reduced glutathion | 0.10 |
| 28 | Phenol red | 0.48 |
| 29 | L-glutamine | 28.70 |
| 30 | Biotin | 0.02 |
| 31 | Calcium D-pantothenate | 0.02 |
| 32 | Folic acid | 0.10 |
| 33 | i-inositol | 3.35 |
| 34 | Nicotinamide | 0.10 |
| 35 | Choline chloride | 0.29 |
| 36 | Pyridoxol hydrochloride | 0.10 |
| 37 | Riboflavin | 0.02 |
| 38 | Thiamine hydrochloride | 0.10 |
| 39 | Vitamin B12 | 0.00 |
| 40 | Fetal bovine serum | 9.57 |

Composition of nutrient ingredient for cells No. 2

| No. | Name of compound | Content (mg) |
|---|---|---|
| 1 | Anhydrous calcium chloride | 26.26 |
| 2 | Iron nitrate nonahydrate | 0.01 |
| 3 | Potassium chloride | 39.64 |
| 4 | Anhydrous magnesium sulfate | 9.68 |
| 5 | Sodium chloride | 634.24 |
| 6 | Anhydrous sodium dihydrogen phosphate | 10.80 |
| 7 | Succinic acid | 7.43 |
| 8 | Sodium succinate | 9.91 |

Composition of nutrient ingredient for cells No. 2 -continued

| No. | Name of compound | Content (mg) |
|---|---|---|
| 9 | L-arginine hydrochloride | 8.32 |
| 10 | L-cystine hydrochloride | 6.24 |
| 11 | Glycine | 2.97 |
| 12 | L-histidine hydrochloride | 4.16 |
| 13 | L-isoleucine | 10.41 |
| 14 | L-leucine | 10.41 |
| 15 | L-lysine hydrochloride | 14.47 |
| 16 | L-methionine | 2.97 |
| 17 | L-phenylalanine | 6.54 |
| 21 | L-serine | 4.16 |
| 22 | L-threonine | 9.41 |
| 23 | L-tryptophan | 1.59 |
| 24 | L-tyrosine | 7.14 |
| 25 | L-valine | 9.32 |
| 26 | Calcium D-pantothenate | 0.40 |
| 27 | Choline bitartrate | 0.71 |
| 28 | Folic acid | 0.40 |
| 29 | Inositol | 0.71 |
| 30 | Nicotinamide | 0.40 |
| 31 | Riboflavin | 0.04 |
| 32 | Thiamine hydrochloride | 0.40 |
| 33 | Pyridoxine hydrochloride | 0.40 |
| 34 | Glucose | 99.10 |
| 35 | Sodium pyruvate | 10.90 |
| 36 | Phenol red | 0.92 |
| 37 | Human serum | 49.55 |

Composition of nutrient ingredient for cells No. 3

| No. | Name of compound | Content (mg) |
|---|---|---|
| 1 | Anhydrous calcium chloride | 13.81 |
| 2 | Iron nitrate nonahydrate | 0.01 |
| 3 | Potassium chloride | 27.61 |
| 4 | Anhydrous magnesium sulfate | 6.74 |
| 5 | Sodium chloride | 441.83 |
| 6 | Anhydrous sodium dihydrogen phosphate | 8.63 |
| 7 | L-arginine hydrochloride | 5.80 |
| 8 | L-cystine hydrochloride | 4.35 |
| 9 | L-glutamine | 40.32 |
| 10 | Glycine | 2.07 |
| 11 | L-histidine hydrochloride | 2.90 |
| 12 | L-isoleucine | 7.25 |
| 13 | L-leucine | 7.25 |
| 14 | L-lysine hydrochloride | 10.08 |
| 15 | L-methionine | 2.07 |
| 16 | L-phenylalanine | 4.56 |
| 17 | L-serine | 2.90 |
| 21 | L-threonine | 6.56 |
| 22 | L-tryptophan | 1.10 |
| 23 | L-tyrosine sodium salt | 7.18 |
| 24 | L-valine | 6.49 |
| 25 | Calcium D-pantothenate | 0.28 |
| 26 | Choline chloride | 0.28 |

Composition of nutrient ingredient for cells No. 3 -continued

| No. | Name of compound | Content (mg) |
|---|---|---|
| 27 | Folic acid | 0.28 |
| 28 | Inositol | 0.50 |
| 29 | Nicotinamide | 0.28 |
| 30 | Riboflavin | 0.03 |
| 31 | Thiamine hydrochloride | 0.28 |
| 32 | Pyridoxine hydrochloride | 0.28 |
| 33 | Glucose | 310.66 |
| 34 | Sodium pyruvate | 7.59 |
| 35 | Phenol red | 1.04 |
| 36 | Albumin | 69.04 |

Composition of nutrient ingredient for cells No. 4

| No. | Name of compound | Content (mg) |
|---|---|---|
| 1 | Anhydrous calcium chloride | 18.21 |
| 2 | Iron nitrate nonahydrate | 0.01 |
| 3 | Potassium chloride | 36.41 |
| 4 | Anhydrous magnesium sulfate | 8.89 |
| 5 | Sodium chloride | 582.59 |
| 6 | Anhydrous sodium dihydrogen phosphate | 11.38 |
| 7 | L-arginine hydrochloride | 7.65 |
| 8 | L-cystine hydrochloride | 5.73 |
| 9 | L-glutamine | 53.16 |
| 10 | Glycine | 2.73 |
| 11 | L-histidine hydrochloride | 3.82 |
| 12 | L-isoleucine | 9.56 |
| 13 | L-leucine | 9.56 |
| 14 | L-lysine hydrochloride | 13.29 |
| 15 | L-methionine | 2.73 |
| 16 | L-phenylalanine | 6.01 |
| 17 | L-serine | 3.82 |
| 21 | L-threonine | 8.65 |
| 22 | L-tryptophan | 1.46 |
| 23 | L-tyrosine sodium salt | 9.47 |
| 24 | L-valine | 8.56 |
| 25 | Calcium D-pantothenate | 0.36 |
| 26 | Choline chloride | 0.36 |
| 27 | Folic acid | 0.36 |
| 28 | Inositol | 0.66 |
| 29 | Nicotinamide | 0.36 |
| 30 | Riboflavin | 0.04 |
| 31 | Thiamine hydrochloride | 0.36 |
| 32 | Pyridoxine hydrochloride | 0.36 |
| 33 | Glucose | 91.03 |
| 34 | Sodium pyruvate | 10.01 |
| 35 | Phenol red | 1.37 |
| 36 | Human serum albumin | 91.03 |

Composition of nutrient ingredient for cells No. 5

| Name of compound | Content (mg) | Name of compound | Content (mg) |
|---|---|---|---|
| Calcium chloride | 8.86 | L-proline | 2.15 |
| Potassium chloride | 17.72 | L-serine | 2.26 |
| Potassium nitrate | 0.00 | L-threonine | 5.10 |
| Anhydrous magnesium sulfate | 5.25 | L-tryptophan | 0.86 |
| Sodium chloride | 241.97 | L-tyrosine | 3.84 |
| Anhydrous sodium dihydrogen phosphate | 5.84 | L-valine | 5.05 |
| Sodium selenite pentahydrate | 0.00 | D-glucose | 241.70 |
| L-alanine | 1.34 | Phenol red | 0.81 |
| L-arginine hydrochloride | 4.51 | HEPES | 320.02 |
| L-asparagine | 1.34 | Sodium pyruvate | 5.91 |
| L-aspartic acid | 1.61 | Vitamin H | 0.00 |
| L-cystine hydrochloride | 4.90 | Nicotinamide | 0.21 |
| L-glutamic acid | 4.03 | Pyridoxal hydrochloride | 0.21 |
| L-glutamine | 31.37 | Calcium D-pantothenate | 0.21 |
| Glycine | 1.61 | Riboflavin | 0.02 |
| L-histidine hydrochloride | 2.26 | Choline chloride | 0.21 |
| L-isoleucine | 5.64 | Thiamine hydrochloride | 0.21 |
| L-leucine | 5.64 | Folic acid | 0.21 |
| L-lysine hydrochloride | 7.84 | i-inositol | 0.39 |
| L-methionine | 1.61 | Vitamin $B_{12}$ | 0.00 |
| L-phenylalanine | 3.54 | Human serum albumin | 53.71 |

Effect Example 1 Comparison of Different Formulations of Cell Cryopreservation Protective Solutions 1. Experiment Design A cell cryopreservation protective solution commonly used in laboratories (80% basal medium+10% DMSO+10% fetal bovine serum, hereinafter sometimes referred to as the conventional protective solution; see Situ Zhenqiang, *Cell Culture*, R. Ian Freshney, *Culture of Animal Cells* and other classic textbooks), as well as glycerol-containing cryoprotectants at different concentrations were used to preserve animal cells, and they were used in comparison with the cell cryopreservation protective compositions comprising zwitterionic molecules having the structure of general formula $R_1-N^+(CH_3)_2-(CH_2)_n-R_2$ provided by the present disclosure in respect of survival rate after cell recovery.

2. Experiment Method (1) Human lung cancer cells GCL-82 were taken and were subjected to subculture; (2) cell cryopreservation protective solutions were prepared according to Table 2 below and cell counting was performed; (3) about $1\times10^6$ cells were collected and suspended in about 1.5 mL to 1.8 mL of cell cryopreservation protective solutions, and the suspensions were added into suitable freezing tubes and directly placed in liquid nitrogen for cryopreservation; (4) after 24 h cryopreservation in liquid nitrogen, the cells were thawed and recovered at 37° C., and were counted by staining using a live/dead cell staining kit (from life technologies, Item No.: L3224), and the survival rates were investigated as follows:

A solution (100 μL) containing a calcein (0.5 mmol/L)/EthD-1 (2 mmol/L) reagent mixture was added to a suspension containing the cells (10 μL), and then the resultant solution was injected into a 96-well TCPS plate to perform staining on the cells; the plate was shielded from light for 30 minutes at room temperature; then an inverted fluorescence microscope (trademark: Nikon Eclipse, type: Ti-S) was used for observation; the number of living cells and the number of dead cells in more than three different samples were calculated to determine cell survival rates. Moreover, human cervical cancer cells HELA and human mammary gland cells MCF-10 were subjected to the same experiment as that described above on the human lung cancer cells GCL-82.

Wherein, the human lung cancer cells GCL-82 and the human lymphatic cancer cells U937 used in the present application are from Tianjin Medical University Cancer Institute and Hospital; the human cervical cancer cells HELA and the human mammary gland cells MCF-10 are from School of Life Sciences, Tianjin University; the human immune cells lymphocyte H9 and the human hematopoietic stem cell are from Tianjin Medical University; the human umbilical cord mesenchymal stem cell and the human bone marrow mesenchymal stem cell are from Chinese Academy of Sciences.

3. Experiment Results

The experiment results are shown in Table 2 and Table 3 below. The experiment results show that in the case where the cell cryopreservation protective solutions are directly placed in liquid nitrogen, the survival rate after cell recovery achieved by using the conventional protective solution is quite low, while the recovery survival rate achieved by using the cell cryopreservation protective compositions comprising zwitterionic molecules having the structure of general formula $R_1-N^+(CH_3)_2-(CH_2)_n-R_2$ provided by the present disclosure is extremely high. Moreover, the cell cryopreservation protective compositions of the present disclosure are safe and non-toxic, and do not require repetitive washing of the cryopreservation protective compositions.

TABLE 2

Recovery survival rate of human lung cancer cells GCL-82 cryopreserved by using different formulations of cryopreservation protective solutions

| Name of cryopreservation protective solution | Component | Content (mass %) | Recovery cell survival rate (%) |
|---|---|---|---|
| Preparation Example 1 | Betaine | 4 | 92.1 |
| Preparation Example 2 | Betaine | 20 | 36.4 |
| Preparation Example 3 | Betaine | 10 | 79.1 |
| Preparation Example 8 | Betaine | 1 | 71.2 |
| Preparation Example 7 | Betaine | 2 | 82.4 |
| Preparation Example 5 | Betaine | 6 | 90.4 |
| Preparation Example 9 | Betaine | 8 | 85.4 |
| Preparation Example 10 | Carboxybetaine (meth)acrylamide | 4 | 88.3 |
| Preparation Example 22 | Sulfobetaine | 4 | 80.5 |
| Preparation Example 28 | Phosphorylcholine derivative | 4 | 82.9 |
| Preparation Example 34 | L-carnitine | 4 | 81.7 |
| Conventional protective solution | (Aqueous) basal medium | 80 | 22.7 |
| | DMSO | 10 | |
| | Fetal bovine serum | 10 | |
| Glycerol cryopreservation protective solution A | Glycerol | 6 | 4.7 |
| | (Aqueous) basal medium | 84 | |
| | Fetal bovine serum | 10 | |
| Glycerol cryopreservation protective solution B | Glycerol | 10 | 7.4 |
| | (Aqueous) basal medium | 80 | |
| | Fetal bovine serum | 10 | |

TABLE 3

Recovery survival rate of human cervical cancer cells HELA and human mammary gland cells MCF-10 cryopreserved by using different formulations of cryopreservation protective solutions

| Name of cryopreservation protective solution (Preparation Example) | Recovery cell survival rate of human cervical cancer cells HELA (%) | Recovery cell survival rate of human mammary gland cells MCF-10 (%) |
|---|---|---|
| Preparation Example 1 | 64.6 | 89.4 |
| Preparation Example 2 | 40.6 | 48.6 |
| Preparation Example 3 | 88.4 | 56.7 |
| Preparation Example 8 | 20.9 | 59.1 |
| Preparation Example 7 | 35.3 | 69.5 |
| Preparation Example 5 | 64.6 | 78.6 |
| Preparation Example 9 | 77.6 | 64.3 |

Effect Example 2 Comparison of Cryopreservation Effects on Different Cell Types

1. Experiment Design

Optimal proportions of the betaine cryopreservation protective compositions in Preparation Examples were used to perform cryopreservation of different types of cells, and the survival rates after cell recovery were compared.

2. Experiment Method (1) Human cell lines were taken and were subjected to subculture; (2) cell cryopreservation protective solutions containing the corresponding betaine cryopreservation protective compositions of optimal proportions, and a conventional protective solution were prepared, and cell counting was performed; (3) about $1\times10^6$ cells were collected and suspended in about 1.5 mL to 1.8 mL of the cell cryopreservation protective solutions, and the suspensions were added into suitable freezing tubes and directly placed in liquid nitrogen for cryopreservation; (4) after 24 h cryopreservation in liquid nitrogen, the cells were thawed and recovered at 37° C., and were counted by staining using a live/dead cell staining kit, and the survival rates were investigated.

3. Experiment Results

The experiment results are shown in Table 4 below. The experiment results show that the cell cryopreservation protective compositions provided by the present disclosure is suitable for various human cell lines, while the conventional protective solution, when used for preservation of various human cell lines by the method of directly placing into liquid nitrogen, results in a quite low recovery cell survival rate.

TABLE 4

Comparison of cryopreservation effects of betaine cryopreservation compositions on different cell types

| Name of cell | Cryopreservation protective solution | Recovery cell survival rate (%) |
|---|---|---|
| Human lung cancer cells GCL-82 | Glycerol cryopreservation protective solution A | 4.7 |
| | Glycerol cryopreservation protective solution B | 7.4 |
| | Conventional protective solution | 22.7 |
| | Cryopreservation protective solution of Preparation Example 1 | 92.1 |
| Human cervical cancer cells HELA | Glycerol cryopreservation protective solution A | 16.7 |
| | Glycerol cryopreservation protective solution B | 26.4 |
| | Conventional protective solution | 1.4 |
| | Cryopreservation protective solution of Preparation Example 3 | 88.4 |
| Human mammary gland cells MCF-10 | Glycerol cryopreservation protective solution A | 31.7 |
| | Glycerol cryopreservation protective solution B | 28.3 |
| | Conventional protective solution | 10.1 |
| | Cryopreservation protective solution of Preparation Example 1 | 89.4 |
| Human umbilical cord mesenchymal stem cells | Glycerol cryopreservation protective solution A | 2.6 |
| | Glycerol cryopreservation protective solution B | 3.1 |
| | Conventional protective solution | 4.2 |
| | Cryopreservation protective solution of Preparation Example 5 | 80.0 |
| Human bone marrow mesenchymal stem cells | Glycerol cryopreservation protective solution A | 5.3 |
| | Glycerol cryopreservation protective solution B | 6.5 |
| | Conventional protective solution | 7.9 |
| | Cryopreservation protective solution of Preparation Example 5 | 85.9 |
| Human lymphatic cancer cells U937 | Glycerol cryopreservation protective solution A | 4.3 |
| | Glycerol cryopreservation protective solution B | 7.9 |
| | Conventional protective solution | 5.8 |
| | Cryopreservation protective solution of Preparation Example 5 | 88.1 |
| Human hematopoietic stem cells | Glycerol cryopreservation protective solution A | 2.1 |
| | Glycerol cryopreservation protective solution B | 2.5 |
| | Conventional protective solution | 5.0 |
| | Cryopreservation protective solution of Preparation Example 5 | 89.6 |
| Human immune cells T lymphocyte H9 | Glycerol cryopreservation protective solution A | 4.1 |
| | Glycerol cryopreservation protective solution B | 5.8 |
| | Conventional protective solution | 8.0 |
| | Cryopreservation protective solution of Preparation Example 5 | 90.2 |

Effect Example 3 Comparison of Cryopreservation Effects at Different Cell Concentrations

1. Experiment Design

The human lung cancer cells GCL-82 at different cell concentrations were cryopreserved by using the cryopreservation protective solution of Preparation Example 1, and the survival rates after cell recovery were compared.

2. Experiment Method (1) Human lung cancer cells GCL-82 were taken and were subjected to subculture; (2) the cryopreservation protective solution of Preparation Example 1 was prepared, and cell counting was performed; (3) about $1\times10^5$ cells, $5\times10^5$ cells, and $1\times10^6$ cells were respectively collected and suspended in about 1.5 mL to 1.8 mL of the cell cryopreservation protective solutions, and the suspensions were added into suitable freezing tubes and directly placed in liquid nitrogen for cryopreservation; (4) after 24 h cryopreservation in liquid nitrogen, the cells were thawed and recovered at 37° C., and were counted by staining using a live/dead cell staining kit, and the survival rates were investigated.

3. Experiment Results

The experiment results are shown in Table 5 below. The experiment results show that the cell cryopreservation protective composition provided by the present disclosure is suitable for cryopreservation at various cell concentrations, and the cryopreservation recovery survival rate is not affected by cell concentration.

TABLE 5

Comparison of cryopreservation effects of the cryopreservation protective solution of Preparation Example 1 on human lung cancer cells GCL-82 at different cell concentrations

| Number of cells | Recovery cell survival rate (%) |
|---|---|
| $1 \times 10^5$ | 92.8 |
| $5 \times 10^5$ | 88.8 |
| $1 \times 10^6$ | 92.1 |

Effect Example 4 Influence of Cryopreservation Time on Cryopreservation Recovery Survival Rate

1. Experiment Design

The human lung cancer cells GCL-82 were cryopreserved by using the cryopreservation protective solution of Preparation Example 1, and the survival rates after cell recovery obtained after different periods of time of cryopreservation were compared.

2. Experiment Method (1) Human lung cancer cells GCL-82 were taken and were subjected to subculture; (2) the cryopreservation protective solution of Preparation Example 1 was prepared and cell counting was performed; (3) about $1\times10^6$ cells were collected and suspended in about 1.5 mL to 1.8 mL of the cell cryopreservation protective solutions, and the suspensions were added into suitable freezing tubes and directly placed in liquid nitrogen for cryopreservation; (4) after designated periods of time of cryopreservation in liquid nitrogen, the cells were thawed and recovered at 37° C., and were counted by staining using a live/dead cell staining kit, and the survival rates were investigated.

3. Experiment Results

The experiment results are shown in Table 6 below. The experiment results show that the cell cryopreservation protective composition provided by the present disclosure can be used for cryopreservation for a long period of time, and it maintains a high cryopreservation recovery survival rate even when the cryopreservation time is long.

TABLE 6

Comparison of cryopreservation effects of the cryopreservation protective solution of Preparation Example 1 on human lung cancer cells GCL-82 after different periods of time of preservation

| Cryopreservation time (day) | Recovery cell survival rate (%) |
|---|---|
| 1 | 92.1 |
| 7 | 84.3 |
| 14 | 90.8 |
| 35 | 82.4 |
| 180 | 85.5 |

Effect Example 5 Influence of Cooling Rate on Cryopreservation Recovery Survival Rate

1. Experiment Design

The human lung cancer cells GCL-82 were cryopreserved with the cryopreservation protective solution of Preparation Example 1 respectively by being subjected to conventional stepwise cooling and being directly placed into liquid nitrogen, and the cell recovery survival rates after cryopreservation at two cooling rates were compared.

2. Experiment Method (1) The human lung cancer cells GCL-82 were taken and were subjected to subculture; (2) the cryopreservation protective solution of Preparation Example 1 was prepared and cell counting was performed; (3) respectively, about $1\times10^6$ cells were collected and suspended in about 1.5 mL to 1.8 mL of the cell cryopreservation protective solutions, and the suspensions were added into two suitable freezing tubes to respectively form sample a and sample b. Sample a was directly placed in liquid nitrogen, while sample b was placed in a stepwise freezing box at 4° C. for 30 minutes, at −20° C. for 90 minutes, and at −80° C. for 10 hours and then transferred into liquid nitrogen for cryopreservation; (4) after 24 h cryopreservation in liquid nitrogen, the cells were thawed and recovered at 37° C., and were counted by staining using a live/dead cell staining kit, and the survival rates were investigated.

3. Experiment Results

The experiment results are shown in Table 7 below. The experiment results show that using the cell cryopreservation protective composition provided by the present disclosure can cryopreserve cells for a long time, and the preservation efficiency will not be drastically reduced due to a slight change in freezing rate.

TABLE 7

Comparison of cryopreservation effects of the cryopreservation protective solution of Preparation Example 1 on human lung cancer cells GCL-82 by methods at different cooling rates

| Sample | Recovery cell survival rate (%) |
|---|---|
| a | 92.1 |
| b | 70.3 |

Effect Example 6 Reattachment of Cells Directly After the Cells are Diluted in Combination with Different Kinds of Cryoprotectants that have been Used for Cryopreservation of the Cells 1. Experiment Design The multiple cell cryopreservation protective solutions of the present application and the conventional DMSO protective solutions were used to perform cryopreservation protective composition-combined dilution and reattachment tests on different kinds of cells. The samples having betaine concentrations of 2%, 6%, and 10% in Effect Examples 6 and 7 are the cell cryopreservation protective solutions in Preparation Example 7, Preparation Example 5, and Preparation Example 3, respectively.

A protective solution having 10% DMSO was prepared according to the composition of the conventional protective solution shown in Table 2. See Table 8 below to obtain the DMSO-containing protective solutions in Effect Examples 6 and 7.

TABLE 8

Compositions of DMSO-containing protective solutions

| Content of component (mass %) | DMSO content 2% | DMSO content 6% | DMSO content 10% |
|---|---|---|---|
| (Aqueous) basal medium | 88 | 84 | 80 |
| DMSO | 2 | 6 | 10 |
| Fetal bovine serum | 10 | 10 | 10 |

2. Experiment Method (1) After 24 h cryopreservation in liquid nitrogen, the cells protected by different cell cryopreservation protective solutions were thawed and recovered at 37° C.; then the cells were diluted in combination with the cryopreservation protective compositions by using the corresponding cell culture media at a volume ratio of 1:4, and injected directly into culture flasks and the flasks were placed in 37° C. and $CO_2$ incubators for culture, and reattachment tests were performed; (2) after 24 h, the culture flasks were taken out, the supernatants were gently pipetted out, and the cell attachment was observed under a microscope.

3. Experiment Results

Figure 2:
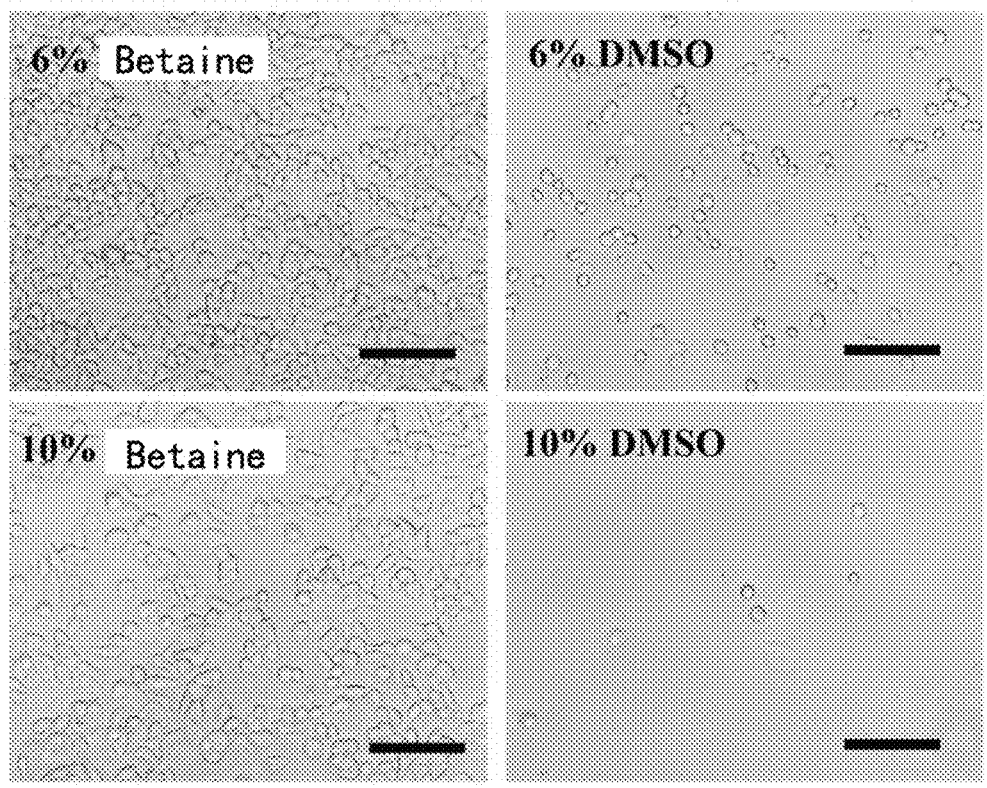
FIG. 2: graphs showing reattachment tests on human lung cancer cells GCL-82 with different cell cryopreservation protective compositions.
Figure 3:
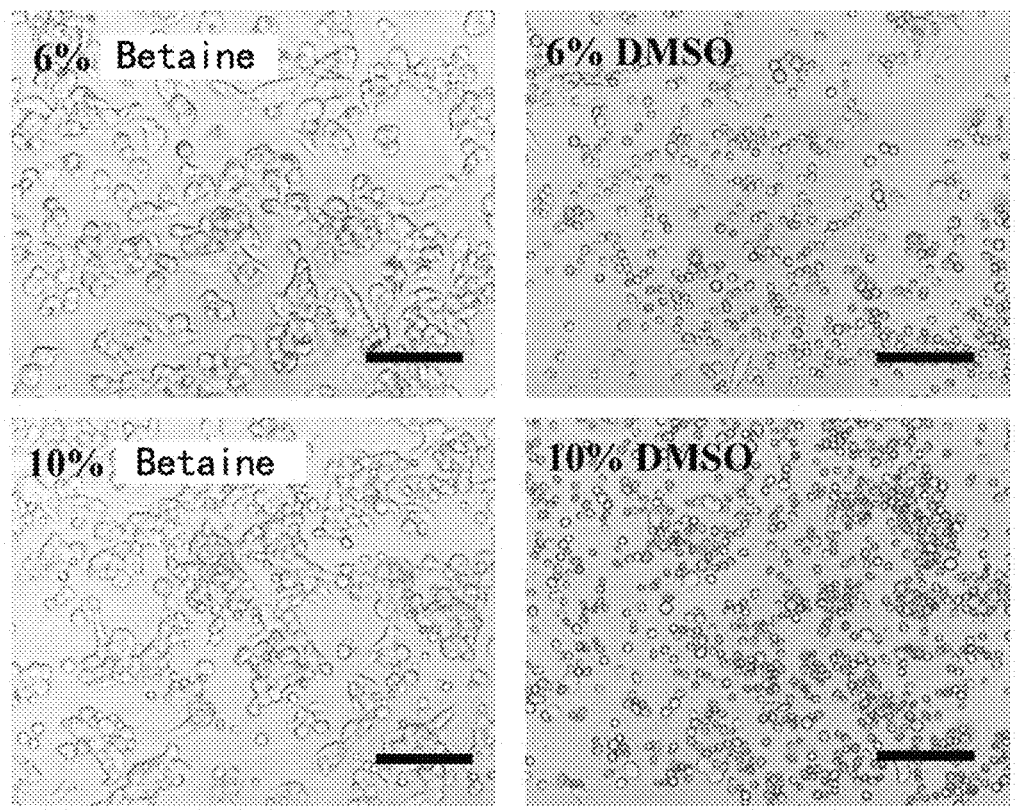
FIG. 3: graphs showing reattachment tests on human cervical cancer cells Hela with different cell cryopreservation protective compositions.
Figure 4:
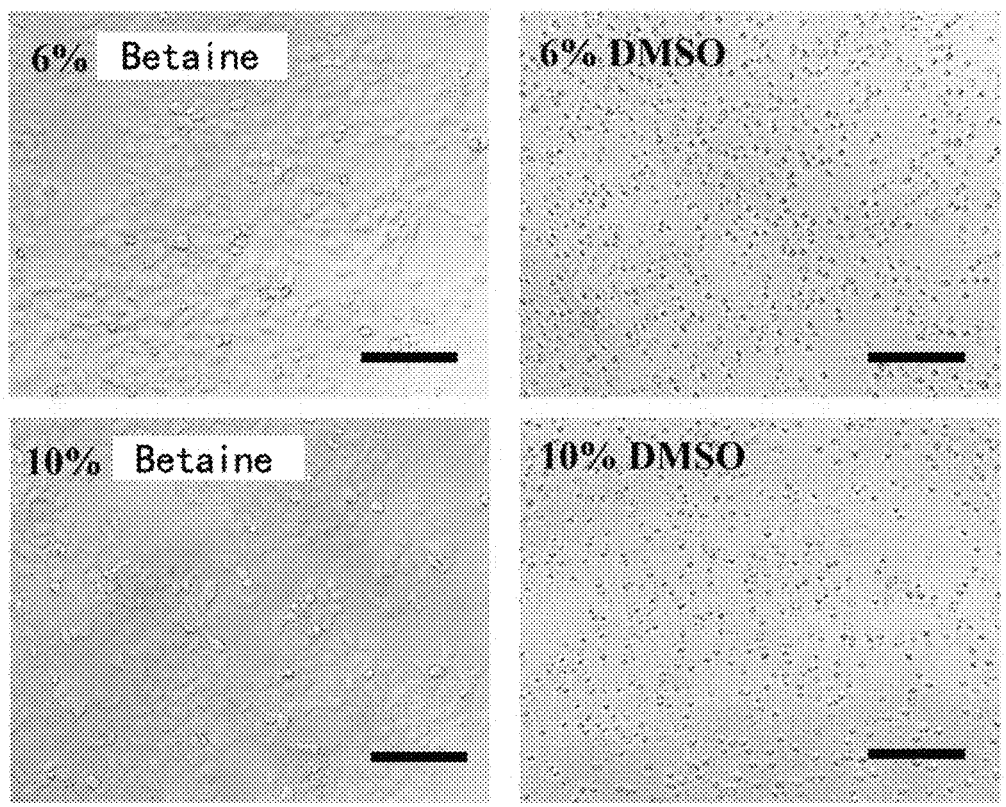
FIG. 4: graphs showing reattachment tests on human mammary gland cells MCF-10 with different cell cryopreservation protective compositions.

The experiment results are shown in FIGS. 2 to 4. FIGS. 2 to 4 show different kinds of cells (human lung cancer cells GCL-82, human cervical cancer cells HELA, and human mammary gland cells MCF-10, respectively) which have been cryopreserved with different cryopreservation protective solutions at the same cell concentration, and then diluted 5 times with the corresponding culture media, and subjected to attachment tests by directly culturing the cells. As shown in the figures, the cells cultured with the cryopreservation protective solutions comprising the betaine-containing cell cryopreservation compositions of the present application can re-attach, and the morphology and proliferation function of the cells are not affected, while the cells cultured with the conventional DMSO protective solution are reduced in size, float above the bottom surface, and cannot attach, and it could be seen from the morphology that the cells have died. The experiment results show that the cell cryopreservation protective solutions provided by the present disclosure are not toxic, can be injected after dilution or directly injected into the body, and the preserved cells have completely normal functions.

Effect Example 7 Cytotoxicity Tests of Cryoprotectants

1. Experiment Design

The cell cryopreservation protective solution of Preparation Example 7 of the present application, a conventional DMSO protective solution and an ordinary culture medium (control) were used to conduct toxicity tests on the same kind of human lung cancer cells, GCL-82 cells.

2. Experiment Method (1) Human lung cancer cells GCL-82 were taken and were subjected to subculture; (2) different cryopreservation protective solutions were prepared and cell counting was performed, and an ordinary culture medium (the volume ratio of basal medium to fetal bovine serum was 8:1) was used as a control group; (3) about $1 \times 10^6$ cells were collected and suspended in a 15 mL centrifuge tube for immersion for 1 to 3 days; (4) the immersed cells were subjected to re-attachment tests.

3. Experiment Results

Figure 5A:
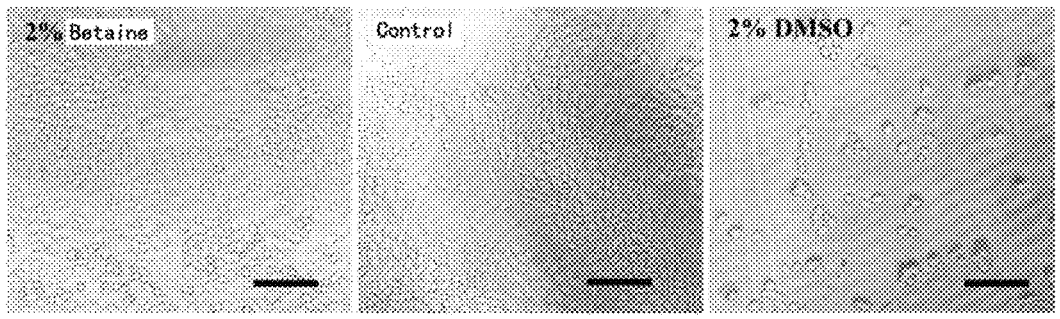
FIG. 5a: graphs showing reattachment tests on human lung cancer cells GCL-82 after 1-day suspension culture with different cell cryopreservation protective compositions.
Figure 5B:
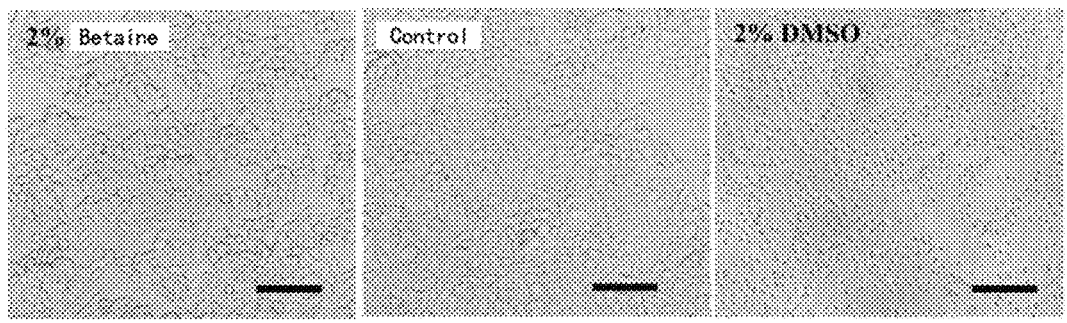
FIG. 5b: graphs showing reattachment tests on human lung cancer cells GCL-82 after 2-day suspension culture with different cell cryopreservation protective compositions.
Figure 5C:
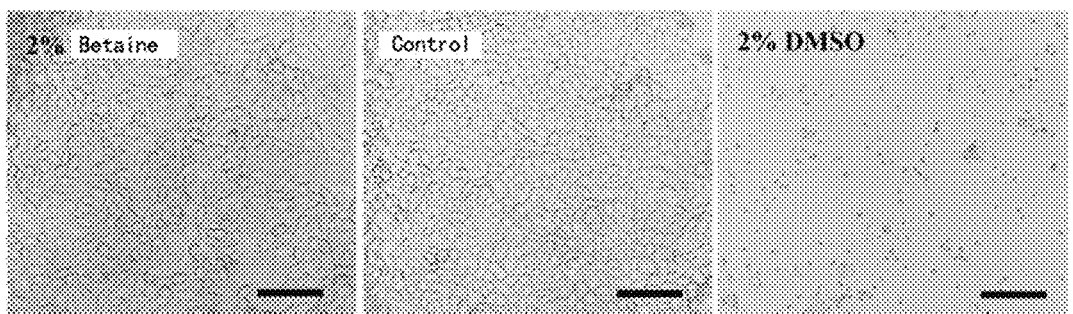
FIG. 5c: graphs showing reattachment tests on human lung cancer cells GCL-82 after 3-day suspension culture with different cell cryopreservation protective compositions.
Figure 6:
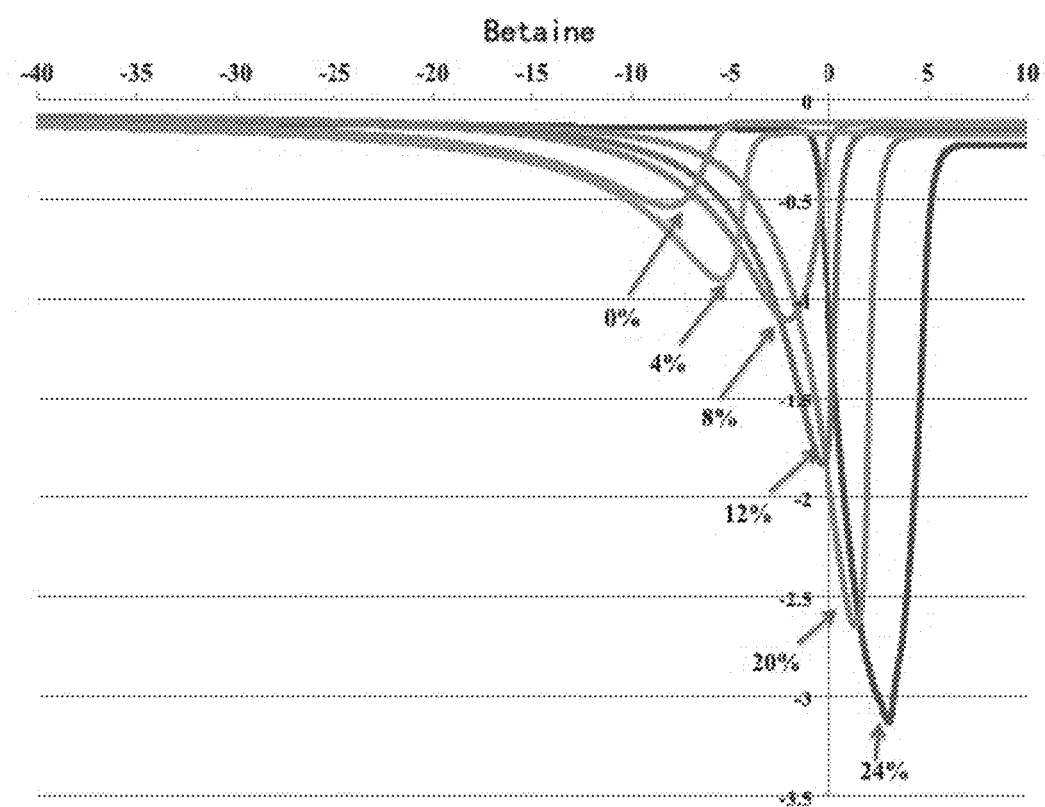
FIG. 6: DSC curves of betaine at different concentrations (mass %).
Figure 7:
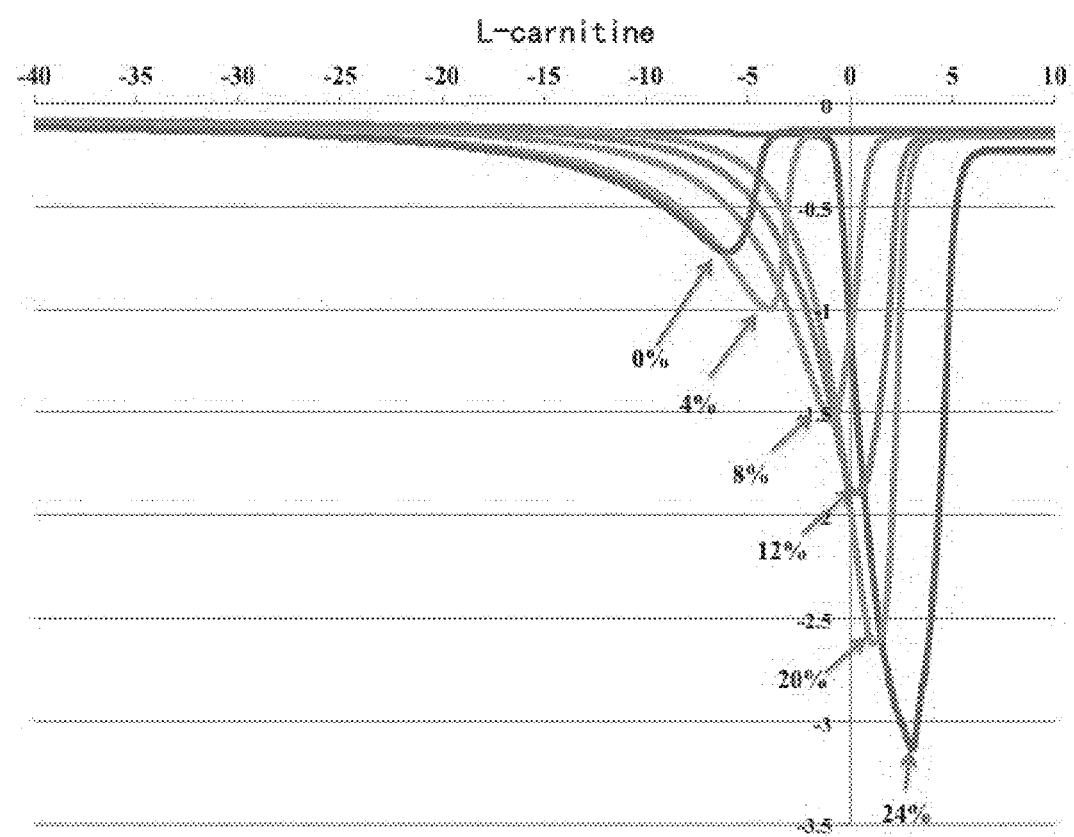
FIG. 7: DSC curves of L-carnitine at different concentrations (mass %).
Figure 8:
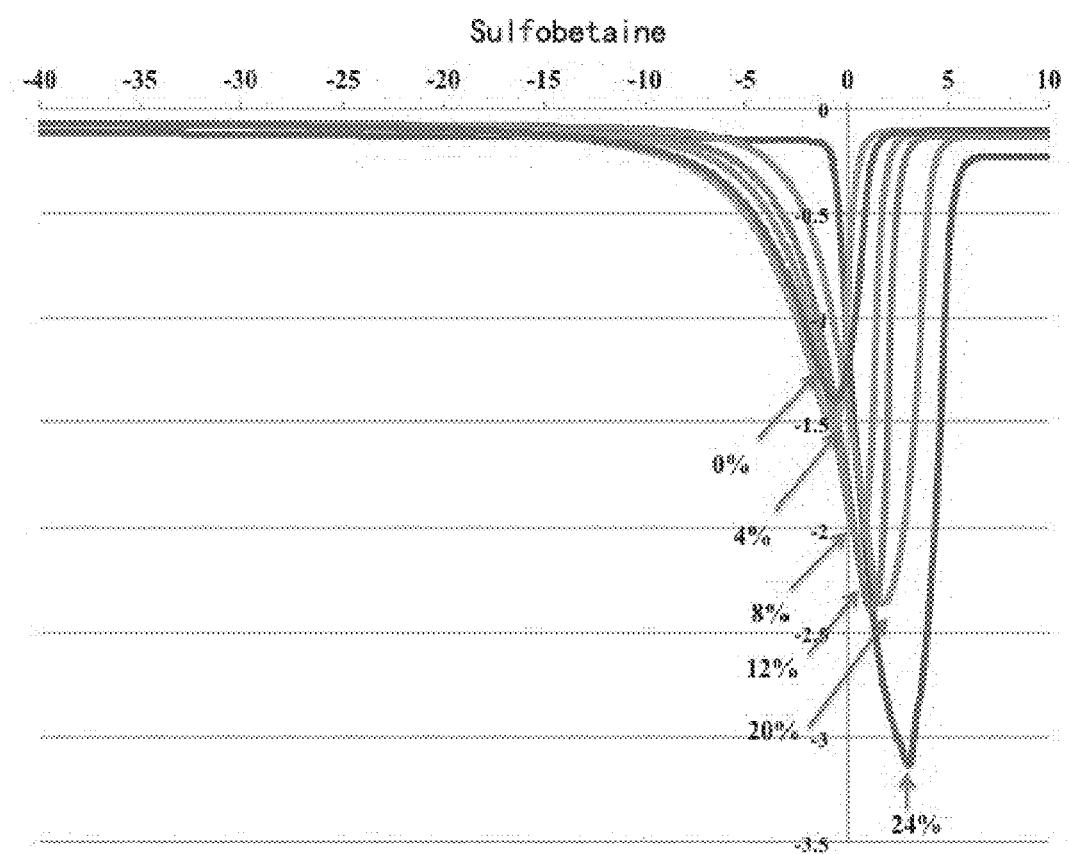
FIG. 8: DSC curves of sulfobetaine at different concentrations (mass %).
Figure 9:
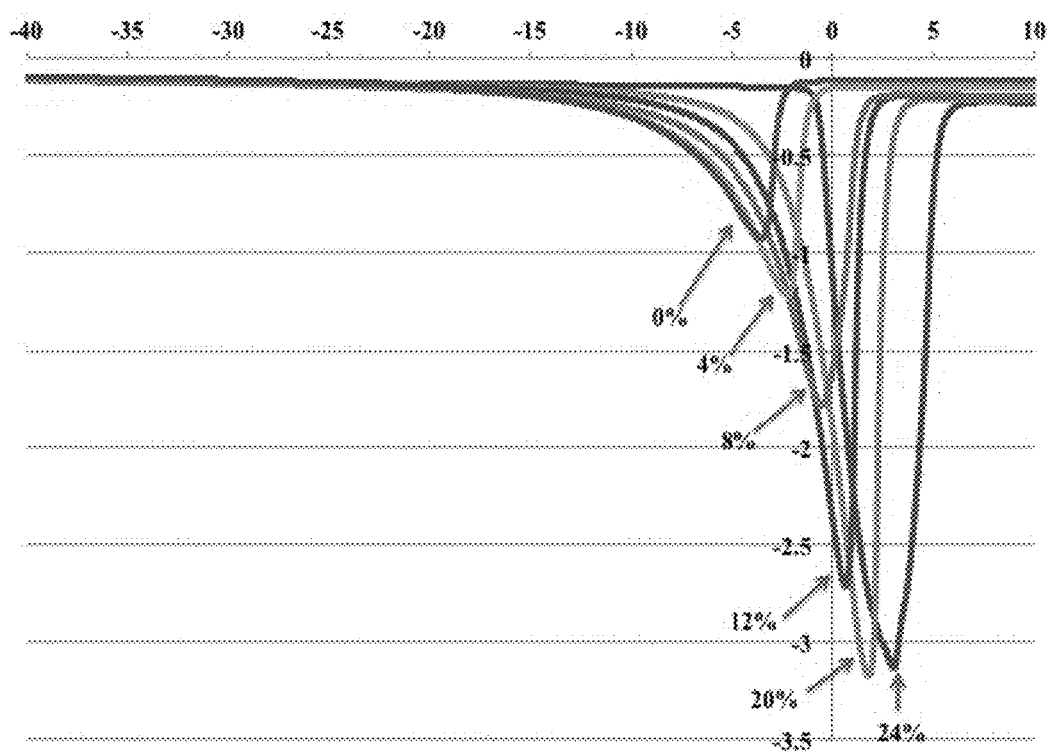
FIG. 9: DSC curves of (3-acryloylaminopropyl)-(2-carboxyethyl)-dimethylammonium at different concentrations (mass %).
Figure 10:
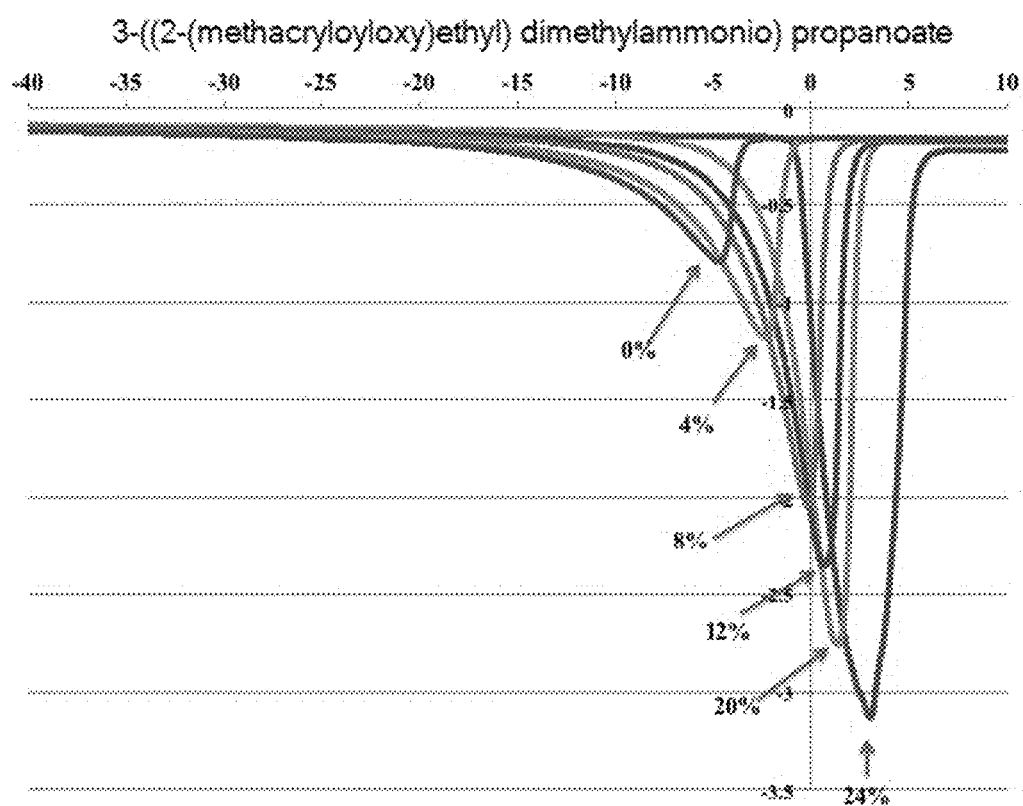
FIG. 10: DSC curves of 3-((2-(methacryloyloxy)ethyl) dimethylammonio) propanoate at different concentrations (mass %).

The experiment results are shown in FIG. 5. FIG. 5 shows attachment tests performed on human lung cancer cells GCL-82 after 1 to 3 days of suspension culture with different cryopreservation compositions at the same cell concentration. As shown in the figure, cells cultured with the cell cryopreservation protective solution containing 2% betaine can re-attach, and their morphology and proliferation function are the same as those subjected to suspension culture with the ordinary culture medium (control); while the cells cultured with the conventional DMSO protective solutions are reduced in size, float above the bottom surface, and cannot attach, and it could be seen from the morphology that the cells have died. The experiment results show that the cell cryopreservation protective solutions provided by the present disclosure has no observable toxicity as compared to the conventional protective solution (DMSO).

Effect Example 8 Tests of Influence Of Cryoprotectants on Freezing Point

DSC means "differential scanning calorimeter", which refers to a technique for measuring, under programmed temperatures, the relationship of temperature and the power difference between an input material and a reference material. DSC was conducted as follows: two sets of compensatory heating wires were installed under the containers of a test sample and a reference material; when a temperature difference $\Delta T$ occurred between the test sample and the reference material due to thermal effect in the process of heating, by a differential thermal amplification circuit and a differential thermal compensation amplifier, the current flowing into the compensatory heating wires was changed; when the test sample absorbed heat, the compensation amplifier immediately increased the current on the side of the test sample, and on the contrary, when the test sample released heat, the current on the side of the reference material increased, until heat balance between both sides was achieved and the temperature difference ΔT disappeared. In other words, the heat change of the test sample, which took place during the thermal reaction, was compensated by the timely input of the electric power, so what was actually recorded was how the thermal power difference between the two sets of electrothermal compensatory heating wires under the test sample and the reference material changed with time t. If the heating rate is constant, it is how the thermal power difference changed with temperature T that is recorded.

Therefore, when the ambient temperature of the test sample rised and the temperature reached the melting point of the sample, an endothermic reaction would take place, and the compensation amplifier would increase the current on the side of the test sample immediately, so a peak value would appear in the curve chart. FIGS. 6 to 10 show DSC curves for respective specific compounds in the aqueous solutions of betaine based compounds at different concentrations, where the abscissa is temperature (° C.), the ordinate is power difference (W/g), and the temperature point where the curve starts to go downwards is the crystallization temperature.

In FIGS. 6 to 10, 0% is pure water. As shown in FIGS. 6 to 10, as the concentrations of effective ingredients increase, the freezing point of water becomes lower, which can prove that the respective specific compounds comprised in betaine based compounds have the effect of lowering the freezing point of water.

Effect Example 9 Recovery Survival Rate of Blood Cells Cryopreserved by Different Cryopreservation Protective Solution Formulations Blood transfusion, also known as "blood transplant", is an important clinical rescue and treatment measure, and is an important method for rescuing patients with traumatic/surgical hemorrhage, as well as for treating aplastic anemia, thalassemia, hemolytic anemia and other diseases. However, once fresh blood is taken from the donor, if it cannot be promptly inputted into patients' bodies, it is necessary to preserve the blood to keep the vitality of the blood cells and maintain the functions that the blood cells should have. At present, the most common method for preserving blood is to place whole blood or blood cells in a protective solution and store the resultant mixture in a refrigerator at 4° C. However, the effective period of this method is only about 42 days, which easily leads to deterioration and waste of blood. Ultra-low temperature cryopreservation can achieve long-term preservation of blood, but currently-used cryopreservation protective solutions still have two main problems: 1. the major component thereof is 40% glycerol, and high concentration of glycerol will increase the risk that the blood cells are subjected to osmotic pressure damage, which is particularly serious in the process of removing the glycerol; 2. the cells need to be preserved in a time-consuming and cumbersome stepwise cooling manner.

1. Experiment Design

Animal cells were preserved with cryoprotectants containing different concentrations of glycerol and DMSO, and were used in comparison with animal cells preserved with the cell cryopreservation protective compositions comprising zwitterionic molecules having the structure of general formula $R_1-N^+(CH_3)_2-(CH_2)_n-R_2$ provided by the present disclosure in respect of survival rate after cell recovery. The cryoprotectants used in this experiment consisted of a buffer equilibrated with the physiological osmotic pressure of human or animal bodies (e.g., physiological saline, phosphate-buffered saline (PBS)), and an effective ingredient for cryopreservation (i.e., the zwitterionic molecules having the structure of general formula $R_1-N^+(CH_3)_2-(CH_2)_n-R_2$ in the present application; or, conventionally used DMSO or glycerol, etc.). That is to say, the cryoprotectants used in this experiment do not require other nutrient ingredients for cells.

2. Experiment Method (1) The respective cell cryopreservation protective solutions (consisting merely of PBS and the effective ingredients for cryopreservation) were prepared according to the following Table 9; (2) about $1 \times 10^7$ sheep blood cells or 20 μL rabbit blood was taken and added into about 1.5 mL to 1.8 mL of the cell cryopreservation protective solutions, and the suspensions were put into suitable freezing tubes and directly placed in liquid nitrogen for cryopreservation; (3) after cryopreservation, the cells were thawed and recovered at 37° C.; the survival rates were investigated by using a microplate reader (trademark: TECAN, model: INFINITE 200 PRO) to determine the hemolysis in each sample, and the method for determining hemolysis is as follows: The recovered samples, a sample of PBS and a sample of water were placed in a centrifuge for centrifugation (2000 r/min, 10 min), and thereafter the supernatants were taken; the light transmittance thereof was measured using the microplate reader and the survival rates of the blood cells were calculated. $1 \times 10^7$ fresh sheep blood cells (or 20 μL rabbit blood) were added to PBS that did not cause hemolysis, and the resultant sample was deemed to have 100% survival rate (positive control group); and the same was added to pure water that certainly would cause hemolysis, and the resultant sample was deemed to have 0% survival rate (negative control group);

Wherein, the sheep blood cells and rabbit blood used in this Effect Example were both purchased from Guangzhou Future Biotechnology Co., Ltd.

3. Experiment Results

The experiment results are shown in Table 9 and Table 10 below. The experiment results show that under the ultrarapid cooling procedures, the cell recovery survival rates of the conventional protective solutions and glycerol protective solutions are quite low; while the cryopreservation protective compositions comprising the zwitterionic molecules having the structure of general formula $R_1-N^+(CH_3)_2-(CH_2)_n-R_2$ provided by the present disclosure achieve extremely high recovery survival rates, and is safe and non-toxic.

TABLE 9

Recovery survival rates of sheep blood cells cryopreserved by different cryopreservation protective solutions

| Effective ingredient | Content of effective ingredient for cryopreservation (mass %) | Recovery cell survival rate (%) |
|---|---|---|
| Betaine | 1 | 25.4 |
| Betaine | 2 | 44.6 |
| Betaine | 3 | 49.3 |

TABLE 9-continued

Recovery survival rates of sheep blood cells cryopreserved by different cryopreservation protective solutions

| Effective ingredient | Content of effective ingredient for cryopreservation (mass %) | Recovery cell survival rate (%) |
|---|---|---|
| Betaine | 4 | 64.8 |
| Betaine | 5 | 70.6 |
| Betaine | 6 | 88.1 |
| Carboxybetaine (meth)acrylamide | 4 | 71.3 |
| Sulfobetaine | 4 | 75.6 |
| Phosphorylcholine derivative | 4 | 80.9 |
| L-carnitine | 6 | 84.0 |
| DMSO | 1 | 8.9 |
| DMSO | 2 | 24.4 |
| DMSO | 3 | 32.4 |
| DMSO | 4 | 44.4 |
| DMSO | 5 | 57.0 |
| DMSO | 6 | 40.8 |
| Glycerol | 1 | 21.7 |
| Glycerol | 2 | 36.5 |
| Glycerol | 3 | 43.5 |
| Glycerol | 4 | 31.8 |
| Glycerol | 5 | 8.8 |
| Glycerol | 6 | 14.4 |
| Glycerol | 10 | 35.8 |
| Glycerol | 40 | 48.0 |

TABLE 10

Recovery survival rates of rabbit blood cryopreserved by different cryopreservation protective solutions

| Effective ingredient | Content of effective ingredient for cryopreservation (mass %) | Recovery cell survival rate (%) |
|---|---|---|
| Betaine | 4 | 55.2 |
| Betaine | 5 | 75.1 |
| Betaine | 6 | 85.4 |
| Betaine | 15 | 89.0 |
| Carboxybetaine (meth)acrylamide | 6 | 65.1 |
| Sulfobetaine | 6 | 73.6 |
| Phosphorylcholine derivative | 6 | 73.9 |
| L-carnitine | 6 | 84.3 |
| Glycerol | 40 | 32.6 |

Effect Example 10 Influence over cell survival rate of washing operation in the process of cryopreserving sheep blood by using betaine at different concentrations (mass %) and glycerol at different concentrations (mass %)

1. Experiment Design

The multiple cell cryopreservation protective solutions of the present application and conventional glycerol protective solutions for blood cells were respectively used to incubate sheep blood cells, and the influence of washing process on the survival rate of sheep blood cells was tested.

2. Experiment Method (1) Equal amounts of sheep blood cells ($1 \times 10^7$ cells) were respectively placed in samples having betaine concentrations of 2%, 4%, and 6% (volume: 1 mL, consisting of betaine and PBS buffer) and samples having glycerol concentrations of 2%, 4%, and 6% (volume: 1 mL, consisting of glycerol and PBS buffer), then the samples were put into a 37° C. and $CO_2$ incubator, being immersed and incubated for 24 hours; (2) after 24 hours, the samples were taken out and diluted 2 folds with PBS, and thereafter the cryoprotectants in the samples were washed away by centrifugation; and the light transmittance of the supernatants was measured by using a microplate reader to calculate the survival rate of blood cells.

3. Experiment Results

Figure 11:
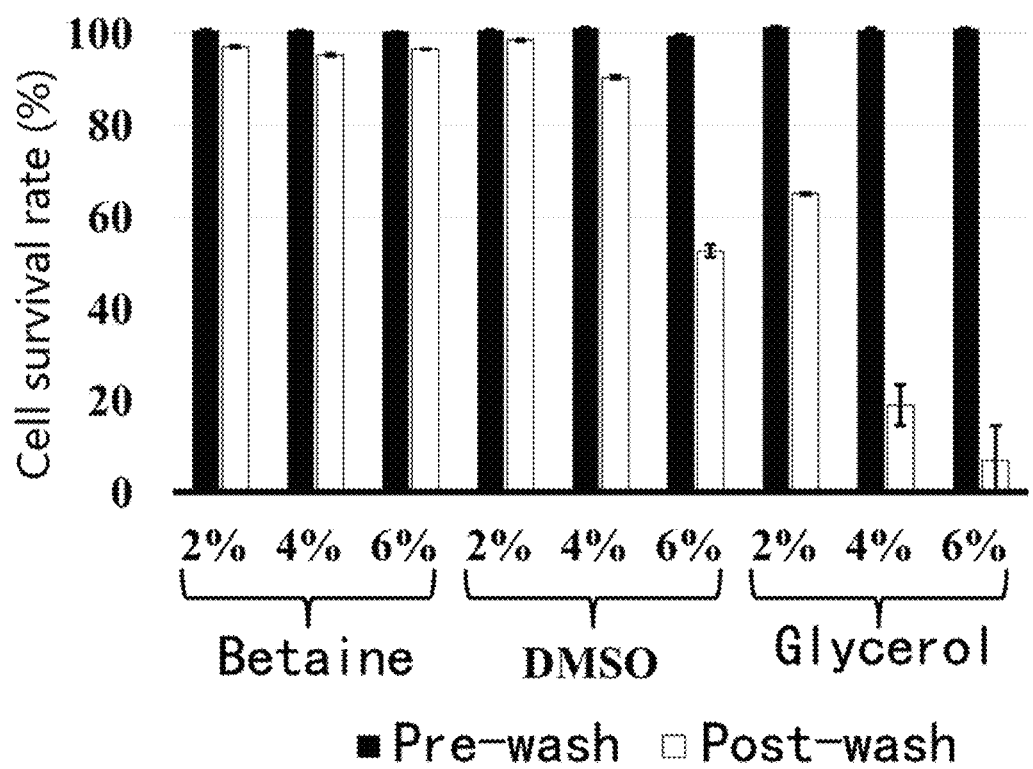
FIG. 11 shows the influence of washing operation on cell survival rate in the process of cryopreserving sheep blood cells by using betaine at different concentrations (mass %), glycerol at different concentrations (mass %), and DMSO at different concentrations (mass %).

The experiment results are shown in FIG. 11. FIG. 11 shows the results of the following experiment: the sheep blood cells were immersed in different cryopreservation protective solutions at the same cell concentration; after 24 h, the samples were taken out, diluted 2 folds with PBS; then, the cryoprotectants in the samples were washed away by centrifugation; and the light transmittance of the supernatants was measured by using a microplate reader to calculate the survival rate of blood cells. As shown in FIG. 11, the survival rates of blood cells before and after washing of the blood cells which have been immersed in the cryopreservation protective solutions containing betaine of the present application are not affected; while the survival rates after dilution and washing of the blood cells which have been immersed in the cryopreservation protective solutions containing glycerol and DMSO drastically decreased, because glycerol cannot be discharge promptly from the cells due to the poor permeability of glycerol, which leads to an imbalance of osmotic pressure inside and outside the cells, and therefore causes hemolysis of a large number of the blood cells; and although the permeability of DMSO is better than that of glycerol, it still causes hemolysis of the blood cells in the washing process. The experiment results show that by using the cell cryopreservation protective solutions provided by the present application, osmotic pressure damage to the blood cells will not occur in the washing process, so these solutions are greatly superior to the currently most effective conventional glycerol and DMSO cryoprotectants. The cryopreservation protective solutions used in Effect Examples 9 and 10 above are consisted of PBS and effective ingredients for cryopreservation only. Nevertheless, it is known that the technical solution obtained in the case where PBS is replaced with a buffer equilibrated with the physiological osmotic pressure of human or animal bodies (e.g., physiological saline, etc.) will also yield a contrast of technical effects similar to that disclosed in Effect Examples 9 and 10.

The above Preparation Examples and Effect Examples are all examples of the specific embodiments and effects of the present disclosure, and should not be construed as limitations on the present disclosure. All the methods disclosed and proposed by the present disclosure can be implemented by those skilled in the art by referring to the contents herein and appropriately changing the raw materials, conditions and the like. Although the methods of the present disclosure have been described in terms of preferred embodiments, it will be apparent to those skilled in the art that various modifications and re-combinations of the methods described herein can be made without departing from the contents, spirit and scope of the present disclosure to implement the final preparation technique. In particular, it should be noted that all similar substitutions and modifications will be apparent to those skilled in the art, and should be deemed to be included within the spirit, scope and contents of the present disclosure.

What is claimed is:

1. A cell cryopreservation protective composition comprising one or more zwitterionic molecules having a structure of general formula $R_1-N^+(CH_3)_2-(CH_2)_n-R_2$, and a nutrient ingredient for cells,
wherein said zwitterionic molecules are 10 to 2530 parts by mass with respect to 100 parts by mass of said nutrient ingredient for cells;
said cell cryopreservation protective composition excludes the following substances: glycerol, diaminoethane tetraacetic acid or salts thereof, dimethyl sulfoxide, or yolk,
in said structure of general formula $R_1-N^+(CH_3)_2-(CH_2)_n-R_2$,
said $R_1$ is linear or branched alkyl having 1 to 10 carbon atoms, and is optionally substituted with a substituent selected from the group consisting of (meth)acryloylamino, (meth)acryloyloxy, alkenyl, hydroxyl, hydroxyalkyl, alkoxyl, and halogen,
said $R_2$ is any negatively charged group selected from the group consisting of $-COO^-$, $-SO_4^-$, $-SO_3^-$, and

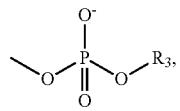

and said $R_3$ is a group selected from the group consisting of (meth)acryloyloxyalkyl, alkyl, and alkenyl,
said $(CH_3)_2$ and $(CH_2)_n$ may each independently be optionally substituted with a substituent selected from the group consisting of alkyl, alkenyl, hydroxyl, hydroxyalkyl, alkoxyl, a polyalkylene oxide group, and halogen, and
n is an integer from 1 to 10,
wherein said nutrient ingredient for cells is selected from the group consisting of one or more of the amino acids arginine, glycine, leucine, glutamine, glutamic acid, isoleucine, and proline.

2. The cell cryopreservation protective composition according to claim 1, wherein in said structure of general formula $R_1-N^+(CH_3)_2-(CH_2)_n-R_2$,
said $R_1$ is linear or branched alkyl having 1 to 5 carbon atoms, and is optionally substituted with a substituent selected from the group consisting of (meth)acryloylamino, (meth)acryloyloxy, hydroxyl, hydroxyalkyl, alkoxyl, and halogen,
said $R_2$ is any group selected from the group consisting of $-COO^-$, $-SO_4^-$, $-SO_3^-$, and

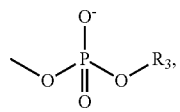

and said $R_3$ is (meth)acryloyloxyalkyl,
the hydrogen atoms in said $(CH_3)_2$ and $(CH_2)_n$ may each independently be optionally substituted with a substituent selected from the group consisting of alkyl, hydroxyl, hydroxyalkyl, alkoxyl, a polyalkylene oxide group, and halogen, and
n is an integer from 1 to 5.

3. The cell cryopreservation protective composition according to claim 2, wherein said zwitterionic molecules are 420 to 1120 parts by mass with respect to 100 parts by mass of said nutrient ingredient for cells; and
in said structure of general formula $R_1-N^+(CH_3)_2-(CH_2)_n-R_2$,
said $R_1$ is linear or branched alkyl having 1 to 3 carbon atoms, and is optionally substituted with a substituent selected from the group consisting of (meth)acryloylamino, (meth)acryloyloxy, hydroxyl, hydroxyalkyl having 1 to 5 carbon atoms, and alkoxyl having 1 to 5 carbon atoms,
the hydrogen atoms in said $(CH_3)_2$ and $(CH_2)_n$ may each independently be optionally substituted with a substituent selected from the group consisting of alkyl having 1 to 5 carbon atoms, hydroxyl, hydroxyalkyl having 1 to 5 carbon atoms, alkoxyl having 1 to 5 carbon atoms, and a polyalkylene oxide group, and
n is an integer from 1 to 3.

4. The cell cryopreservation protective composition according to claim 1, wherein 100 parts by mass of said nutrient ingredient for cells comprise components of the following parts by mass:

| | |
|---|---|
| the one or more amino acids | 5 to 15 parts; |
| one or more salts | 45 to 75 parts; |
| one or more saccharides | 8 to 32 parts; |
| one or more vitamins | 0.1 to 1.0 part; and |
| one or more proteins | 0.5 to 10 parts. |

5. The cell cryopreservation protective composition according to claim 1, wherein said zwitterionic molecule having the structure of general formula $R_1-N^+(CH_3)_2-(CH_2)_n-R_2$ is $CH_3-N^+(CH_3)_2-CH_2-COO^-$.

6. The cell cryopreservation protective composition according to claim 1, wherein in the zwitterionic molecule having the structure of general formula $R_1-N^+(CH_3)_2-(CH_2)_n-R_2$, the hydrogen atom in $(CH_2)_n$ is substituted with hydroxyl and $R_2$ is $-COO^-$.

7. The cell cryopreservation protective composition according to claim 1, wherein said cell cryopreservation protective composition is used for protecting human cells or mammalian cells during cryopreservation.

8. The cell cryopreservation protective composition according to claim 7, wherein said human cells or mammalian cells comprise at least one of cancer cells, somatic cells, and stem cells.

9. The cell cryopreservation protective composition according to claim 8, wherein said somatic cells are immune cells or blood cells.

10. The cell cryopreservation protective composition according to claim 7, wherein said human cells comprise at least one of lung cancer cells, cervical cancer cells, mammary gland cells, hematopoietic stem cells, immune cells, umbilical cord mesenchymal stem cells, bone marrow mesenchymal stem cells, lymphatic cancer cells, and blood cells.

11. A cell cryopreservation protective solution which is an aqueous solution of the cell cryopreservation protective composition according to claim 1, wherein the content of the zwitterionic molecules in the cell cryopreservation protective solution is 0.1 to 20 mass %, based on the total mass of the cell cryopreservation protective solution.

12. The cell cryopreservation protective solution according to claim 11, wherein the content of the zwitterionic molecules in the cell cryopreservation protective solution is 4 to 10 mass %, based on the total mass of the cell cryopreservation protective solution.

13. A method of cryopreserving cells, comprising: suspending cells in the cell cryopreservation protective solution according to claim 11, placing the solution in a cryopreservation container, and then performing cryopreservation.

14. The method according to claim 13, wherein said cryopreservation is ultrarapid cryopreservation.

15. The method of cryopreserving cells according to claim 13, wherein after said cryopreservation is performed, the cryopreserved cells are recovered, and then said cells are used directly or said cells are used in a diluted manner.

16. The method according to claim 13, wherein the recovery survival rate of said cells is at least 70%.

17. The method according to claim 13, wherein cells are suspended in said cell cryopreservation protective solution at a concentration that $1\times10^4$ to $1\times10^9$ cells are suspended in 1.0 mL to 5.0 mL of said cell cryopreservation protective solution.

18. The method according to claim 13, wherein the temperature range of the cryopreservation is −20° C. to −196° C.

* * * * *